US008056557B2

(12) United States Patent
Lieberman et al.

(10) Patent No.: US 8,056,557 B2
(45) Date of Patent: Nov. 15, 2011

(54) NEBULIZING DRUG DELIVERY DEVICE WITH BARRIER

(75) Inventors: Eric A. Lieberman, Scotch Plains, NJ (US); Dirk Von Hollen, Clark, NJ (US); Alexandru Bucur, Norcross, GA (US); Lev Pavlovsky, Morris Plains, NJ (US)

(73) Assignee: RIC Investments, LLC, Wilmington, DE (US)

( * ) Notice: Subject to any disclaimer, the term of this patent is extended or adjusted under 35 U.S.C. 154(b) by 481 days.

(21) Appl. No.: 11/367,075

(22) Filed: Mar. 3, 2006

(65) Prior Publication Data

US 2006/0243274 A1 Nov. 2, 2006

Related U.S. Application Data

(60) Provisional application No. 60/659,781, filed on Mar. 9, 2005.

(51) Int. Cl.

| | |
|---|---|
| *A61M 15/00* | (2006.01) |
| *A61M 16/00* | (2006.01) |
| *A61M 11/00* | (2006.01) |
| *A61M 16/10* | (2006.01) |
| *B05B 17/06* | (2006.01) |

(52) U.S. Cl. ......... 128/200.16; 128/200.14; 128/203.12; 128/203.15; 128/200.24

(58) Field of Classification Search ............. 128/200.11, 128/200.13, 200.14, 200.16, 200.21, 200.24; 222/420, 135, 161; 239/102.1, 102.2, 338, 239/4
See application file for complete search history.

(56) References Cited

U.S. PATENT DOCUMENTS

| | | | | |
|---|---|---|---|---|
| 3,387,607 | A * | 6/1968 | Gauthier et al. | 128/200.16 |
| 3,433,461 | A * | 3/1969 | Scarpa | 366/112 |
| 3,490,697 | A | 1/1970 | Best, Jr. | |
| 3,806,100 | A * | 4/1974 | Cornett et al. | 261/1 |
| 3,918,641 | A | 11/1975 | Lehmann et al. | |
| 4,094,317 | A * | 6/1978 | Wasnich | 128/200.16 |
| 4,113,809 | A * | 9/1978 | Abair et al. | 261/81 |
| 4,200,093 | A | 4/1980 | Camp | |
| 4,656,707 | A * | 4/1987 | Berte et al. | 29/25.35 |
| 4,820,453 | A | 4/1989 | Huang | |
| 4,951,661 | A | 8/1990 | Sladek | |
| 4,976,259 | A * | 12/1990 | Higson et al. | 128/200.18 |
| 5,062,419 | A | 11/1991 | Rider | |
| 5,277,175 | A | 1/1994 | Riggs et al. | |
| 5,308,180 | A * | 5/1994 | Pournoor et al. | 401/205 |
| 5,361,989 | A * | 11/1994 | Merchat et al. | 239/102.2 |
| 5,429,302 | A * | 7/1995 | Abbott | 239/102.2 |

(Continued)

FOREIGN PATENT DOCUMENTS

AU 2003254386 B2 * 10/2006

(Continued)

*Primary Examiner* — Justine Yu
*Assistant Examiner* — Annette Dixon
(74) *Attorney, Agent, or Firm* — Timothy Nathan

(57) ABSTRACT

The present invention provides a drug delivery device that uses an aerosol generator to nebulize a drug solution. The drug delivery device includes differently sized guide tubes and separator walls to provide substantially consistent particles that can be varied in size by using different guide tubes. The drug delivery device also includes a barrier that separates a fluid contained in the device from the drug solution at least a portion of the barrier is formed from Polyetheretherketone. The present invention also has a drug detection device that can detect the volume of drug in the device or whether the barrier has been compromised.

7 Claims, 34 Drawing Sheets

U.S. PATENT DOCUMENTS

| | | | |
|---|---|---|---|
| 5,485,827 A | 1/1996 | Zapol et al. | |
| 5,646,470 A * | 7/1997 | de Groot | 310/337 |
| 5,687,715 A | 11/1997 | Landis et al. | |
| 5,707,352 A | 1/1998 | Sekins et al. | |
| 5,724,965 A | 3/1998 | Handke et al. | |
| 5,756,994 A * | 5/1998 | Bajic | 250/288 |
| 5,865,171 A | 2/1999 | Cinquin | |
| 5,908,158 A | 6/1999 | Cheiman | |
| 6,152,383 A * | 11/2000 | Chen | 239/102.2 |
| 6,202,642 B1 | 3/2001 | McKinnon et al. | |
| 6,234,167 B1 | 5/2001 | Cox et al. | |
| 6,241,162 B1 * | 6/2001 | Takahashi et al. | 239/102.2 |
| 6,283,118 B1 | 9/2001 | Lu | |
| 6,328,030 B1 | 12/2001 | Kidwell et al. | |
| 6,357,671 B1 * | 3/2002 | Cewers | 239/102.2 |
| 6,402,046 B1 | 6/2002 | Loser | |
| 6,443,146 B1 | 9/2002 | Voges | |
| 6,478,754 B1 | 11/2002 | Babaev | |
| 6,516,802 B2 | 2/2003 | Hansen et al. | |
| 6,530,570 B2 | 3/2003 | Ku | |
| 6,550,476 B1 | 4/2003 | Ryder | |
| 6,628,798 B2 * | 9/2003 | Teshima et al. | 381/396 |
| 6,640,804 B2 | 11/2003 | Irvi et al. | |
| 6,727,466 B2 | 4/2004 | Mayo et al. | |
| 6,854,465 B2 | 2/2005 | Bordewick et al. | |
| 7,059,320 B2 * | 6/2006 | Feiner et al. | 128/200.16 |
| 7,089,941 B2 | 8/2006 | Bordewick et al. | |
| 7,211,320 B1 * | 5/2007 | Cooper et al. | 428/306.6 |
| 2002/0011248 A1 | 1/2002 | Hansen et al. | |
| 2002/0082666 A1 | 6/2002 | Babaev | |
| 2003/0205229 A1 | 11/2003 | Crockford et al. | |
| 2004/0025882 A1 | 2/2004 | Madaus et al. | |
| 2005/0042170 A1 | 2/2005 | Jiang et al. | |
| 2006/0201500 A1 | 9/2006 | Von Hollen et al. | |
| 2006/0201502 A1 | 9/2006 | Lieberman et al. | |
| 2006/0243274 A1 | 11/2006 | Lieberman et al. | |

FOREIGN PATENT DOCUMENTS

| | | |
|---|---|---|
| RU | 2070062 | 12/1996 |
| RU | 2076746 | 4/1997 |
| WO | WO95/26236 A1 | 10/1995 |
| WO | WO-03/035152 A1 | 5/2003 |
| WO | WO 2004/017848 | 3/2004 |

* cited by examiner

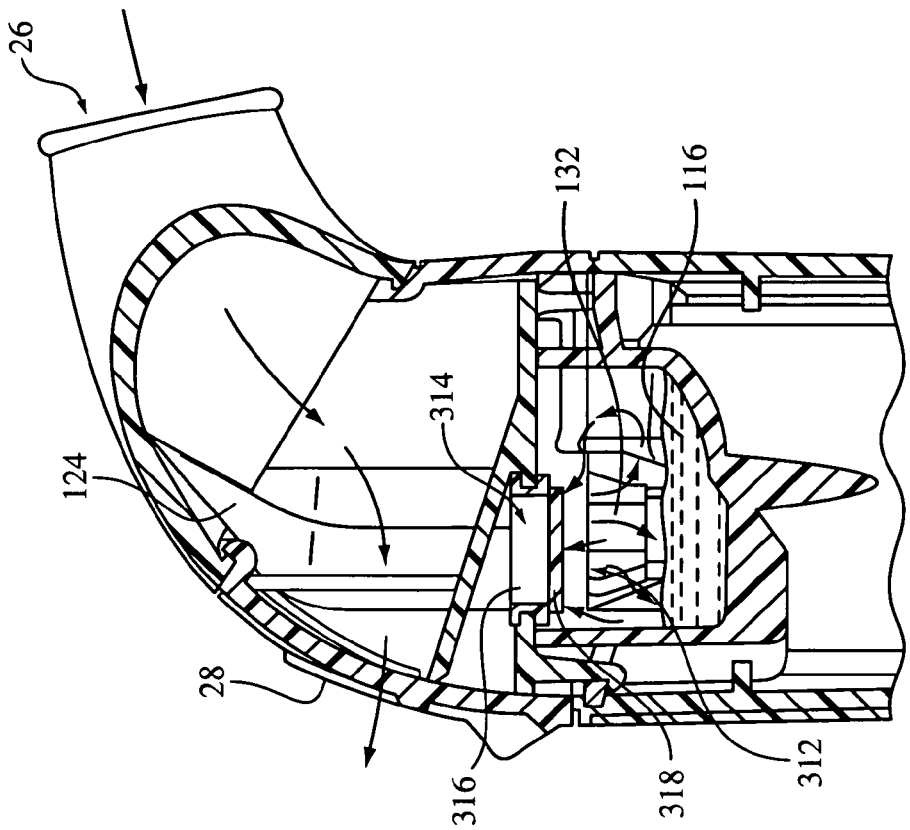
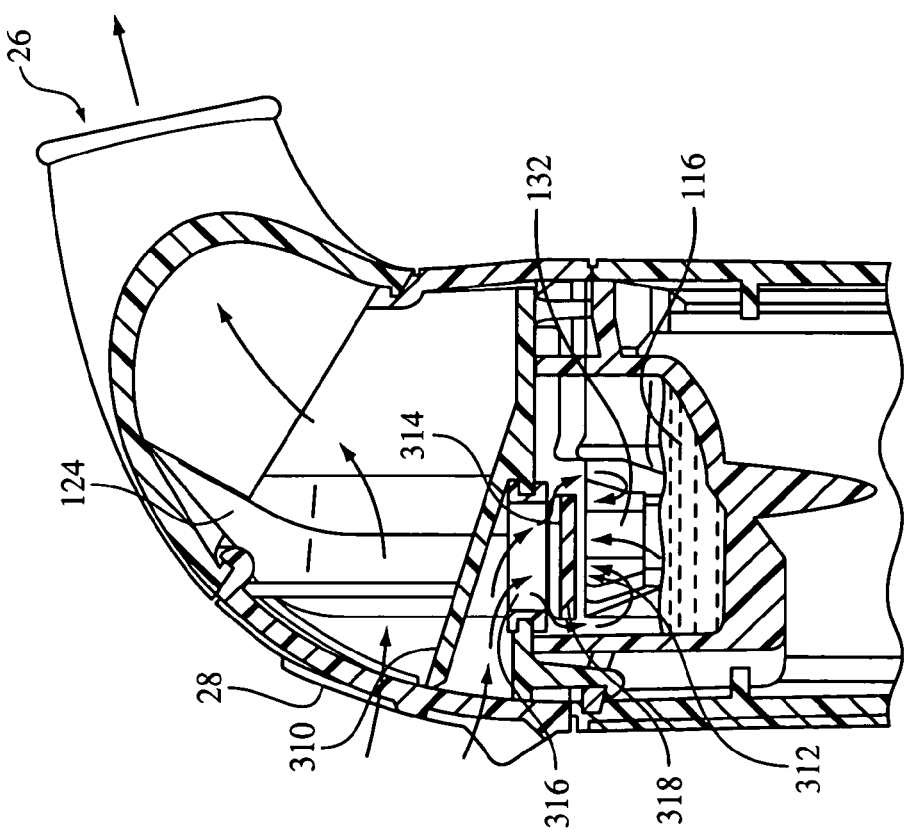
FIG. 4A
FIG. 4B

FIG. 24

```
                    ┌─────────────┐
                    │ ACTIVATION  │──2510
                    │  COMMAND    │
                    └──────┬──────┘
                           │
                      2512 │
┌─────────────┐           ◇
│ DEACTIVATE  │    NO   ╱PROPERLY╲
│  AEROSOL    │◄───────╱ COUPLED  ╲
│  GENERATOR  │        ╲    ?     ╱
└─────────────┘         ╲        ╱
   2514                      │ YES
                       2516  │
                    ┌─────────────┐
                    │  ACTIVATE   │
                    │  AEROSOL    │
                    │  GENERATOR  │
                    └──────┬──────┘
                           │
                           ▼   2518
                   NO   ╱  DRUG  ╲
              ◄────────╱ PRESENT ╲
                       ╲    ?    ╱
                        ╲       ╱
                           │ YES
                           ▼   2520
                   YES  ╱DEACTIVATION╲
              ◄────────╱   COMMAND    ╲
                       ╲      ?       ╱
                        ╲            ╱
                           │ NO
                           ▼    2522
                   YES  ╱  TIME  ╲
              ◄────────╱   OUT    ╲──────┐
                       ╲    ?     ╱      │
                        ╲        ╱       │
                           │ NO          │
                           └─────────────┘
```

FIG. 25

NEBULIZING DRUG DELIVERY DEVICE WITH BARRIER

CROSS-REFERENCE TO RELATED APPLICATIONS

This application claims priority under 35 U.S.C. §119(e) from provisional U.S. Patent Application Ser. No. 60/659,781 filed Mar. 9, 2005 the contents of which are incorporated herein by reference.

BACKGROUND OF THE INVENTION

1. Field of the Invention

The present invention relates to drug delivery devices, and, in particular, to drug delivery devices that utilize an aerosol generator to nebulize a drug solution.

2. Description of the Related Art

Conventional ultrasonic drug nebulizing devices nebulize a drug solution by transmitting acoustic waves from an acoustic wave generator to the drug solution. Some of these devices transmit the acoustic waves from the acoustic wave generator to the drug solution through a fluid. Typically, these devices provide a barrier between the fluid and the drug solution. The barrier seals the drug solution from communication with the fluid, and also allows the acoustic waves from the aerosol generator to pass therethrough, from the transmitting fluid to the drug solution.

These barriers are typically composed of materials such as metal, which are generally considered suitable because their thermal and mechanical properties enable them to partially transmit the ultrasonic energy present in the acoustic waves from the fluid to the drug solution. However, known barrier materials like metallic materials still do not transmit all of the ultrasonic energy transmitted from the generator to the barrier, and therefore, form an energy sink within the device. This inhibits various aspects of the operation of typical nebulizing devices, such as, for example, nebulizing efficiency, flow rate, and the range of drug viscosities that can be nebulized.

Additionally, barrier materials are usually limited to materials that can be formed into a barrier and installed securely into nebulizing devices. Consequently, various materials that may provide enhanced barriers have not been used because there has not been a suitable mechanism for disposing a barrier composed of such materials within a nebulizing device.

In addition, for some materials the relative thickness and/or structural attributes of the barrier require careful balancing. The material should have sufficient structural integrity and strength to permit it to be securely sealed between the transmitting fluid and drug solution, yet at the same time sufficiently thin and flexible to transmit acoustic (ultrasonic) waves from the transmitting fluid to the drug solution. Heretofore, this balance has only been achieved with limited success.

SUMMARY OF THE INVENTION

In accordance with the broad teachings of the invention, one aspect of the present invention relates to a nebulizing device comprising a housing having an inlet and an outlet, an aerosol generator in communication with a fluid, and a barrier between the fluid and a drug solution provided within the housing. The aerosol generator operates to form nebulized particles of the drug solution that can be communicated to a user through the outlet. The barrier is formed from polyetheretherketone.

Another aspect of the invention relates to a nebulizing device comprising a housing having an inlet and an outlet, an aerosol generator in communication with a fluid, a barrier between the fluid, and a drug solution provided in the housing. The aerosol generator operates to form nebulized particles from the drug solution that can be communicated to a user through the outlet. The housing contains therein a mounting surface on which the barrier is mounted. The barrier has a peripheral portion thereof with a greater thickness than a central portion thereof, the peripheral portion being secured to the mounting surface.

In one embodiment, the barrier is formed from two parts, including a first part having an opening therethrough. The opening generally defines the central portion of smaller thickness, and a second part covers the opening, with the first part being sealed with the second part.

In one embodiment, the peripheral portion of the barrier has a plurality of holes formed therein, and the mounting surface comprises a plurality of projections that are received within the holes. The projections are deformed in a manner that secures the barrier to the mounting surface.

Another aspect of the invention relates to a method of assembling a nebulizing device comprising forming a housing having an inlet and an outlet, forming an aerosol generator within the housing, forming a barrier that includes a peripheral portion thereof with a greater thickness than a central portion thereof, disposing the barrier within the housing, and introducing a fluid between the aerosol generator and the barrier. The aerosol generator operates to form nebulized particles from the drug solution that can be communicated to a user through the outlet.

In some embodiments, forming the peripheral portion of the barrier and the central portion of the barrier comprises securing a first part to a second part, the first part having an opening therethrough, the opening generally defining the central portion of smaller thickness, and the second part covering the opening.

In one embodiment, mounting the peripheral portion of the barrier to the mounting surface comprises forming a plurality of projections at the mounting surface, forming a plurality of holes in the peripheral portion, introducing the barrier to the mounting surface such that the plurality of holes receive the plurality of projections, and deforming the plurality of projections in a manner that secures the barrier to the mounting surface.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

A specific embodiment of the invention is now described with reference to the accompanying drawings, wherein:

FIGS. 4A and 4B are partial cross-sectional views taken along line 4-4 of FIG. 1B which illustrate an air flow through the nebulizing device according to an embodiment of the invention.

FIG. 24 is a schematic representation of the circuitry of the drug delivery device according to one embodiment of the invention.

FIG. 25 is an exemplary illustration of a method of control the drug delivery device in accordance with an embodiment of the invention.

DETAILED DESCRIPTION OF THE PRESENTLY PREFERRED EMBODIMENTS OF THE INVENTION

Figure 1A:
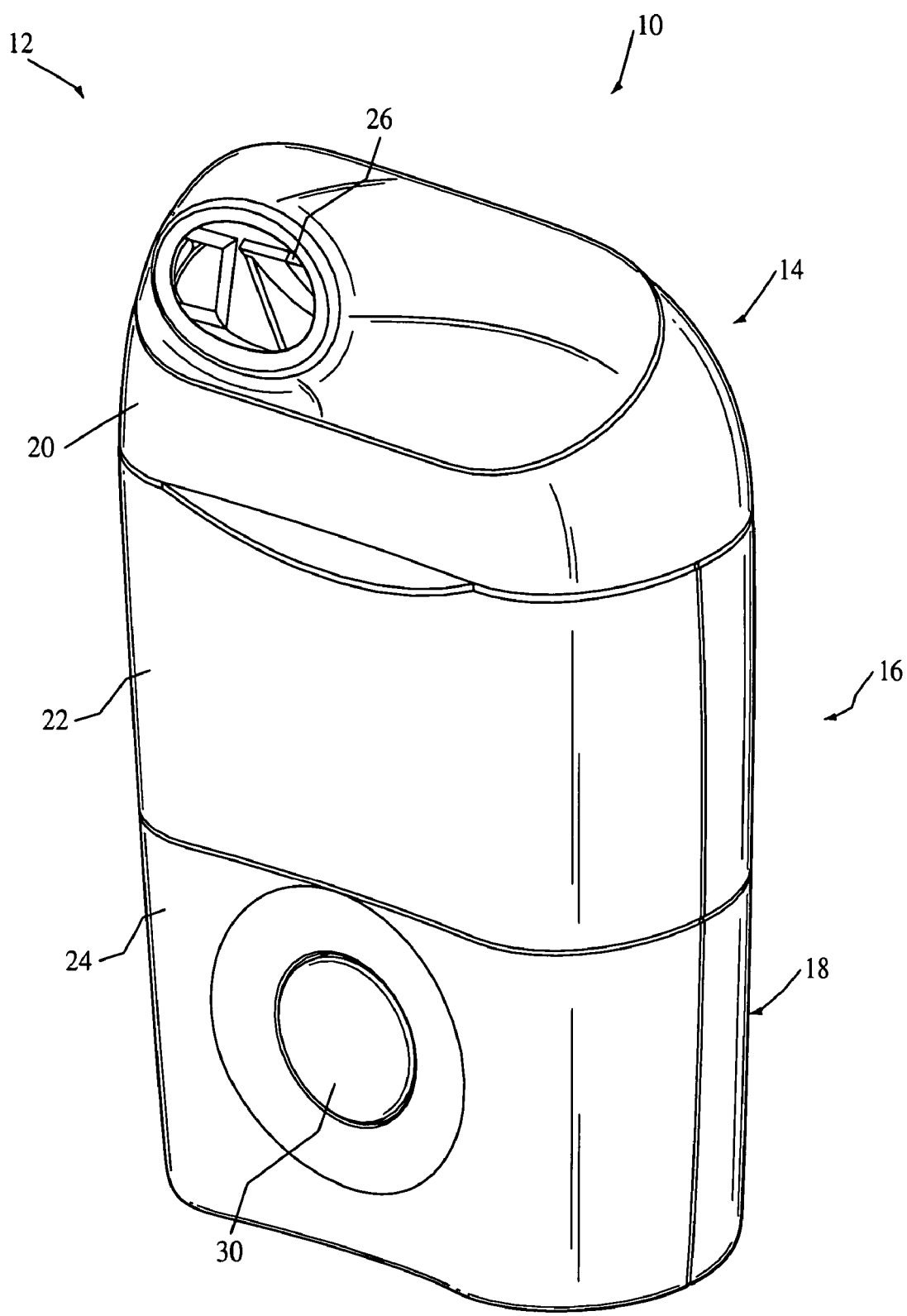
FIG. 1A-1C are perspective and elevational views of the nebulizing device according to an embodiment of the invention.
Figure 1B:
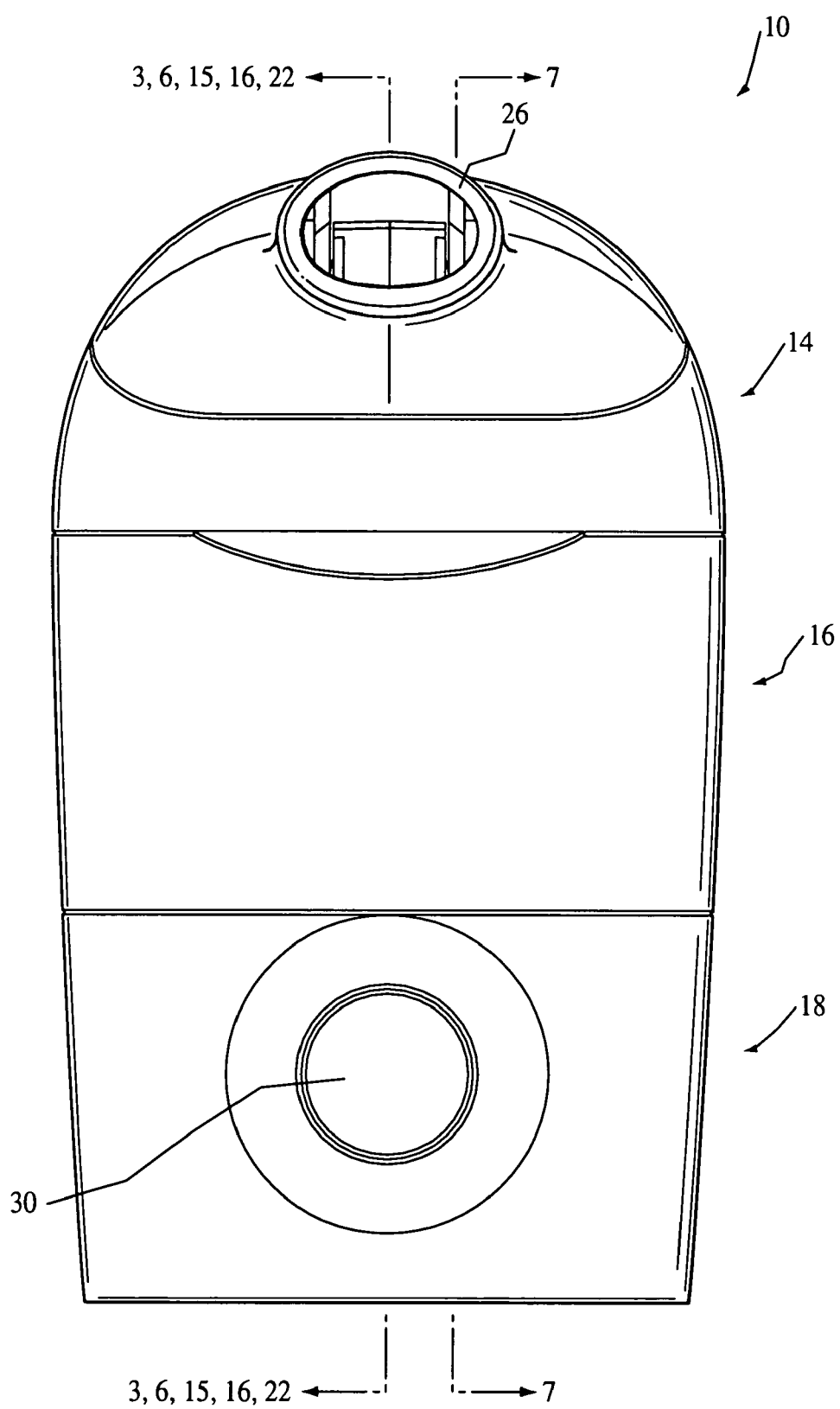
Figure 1C:
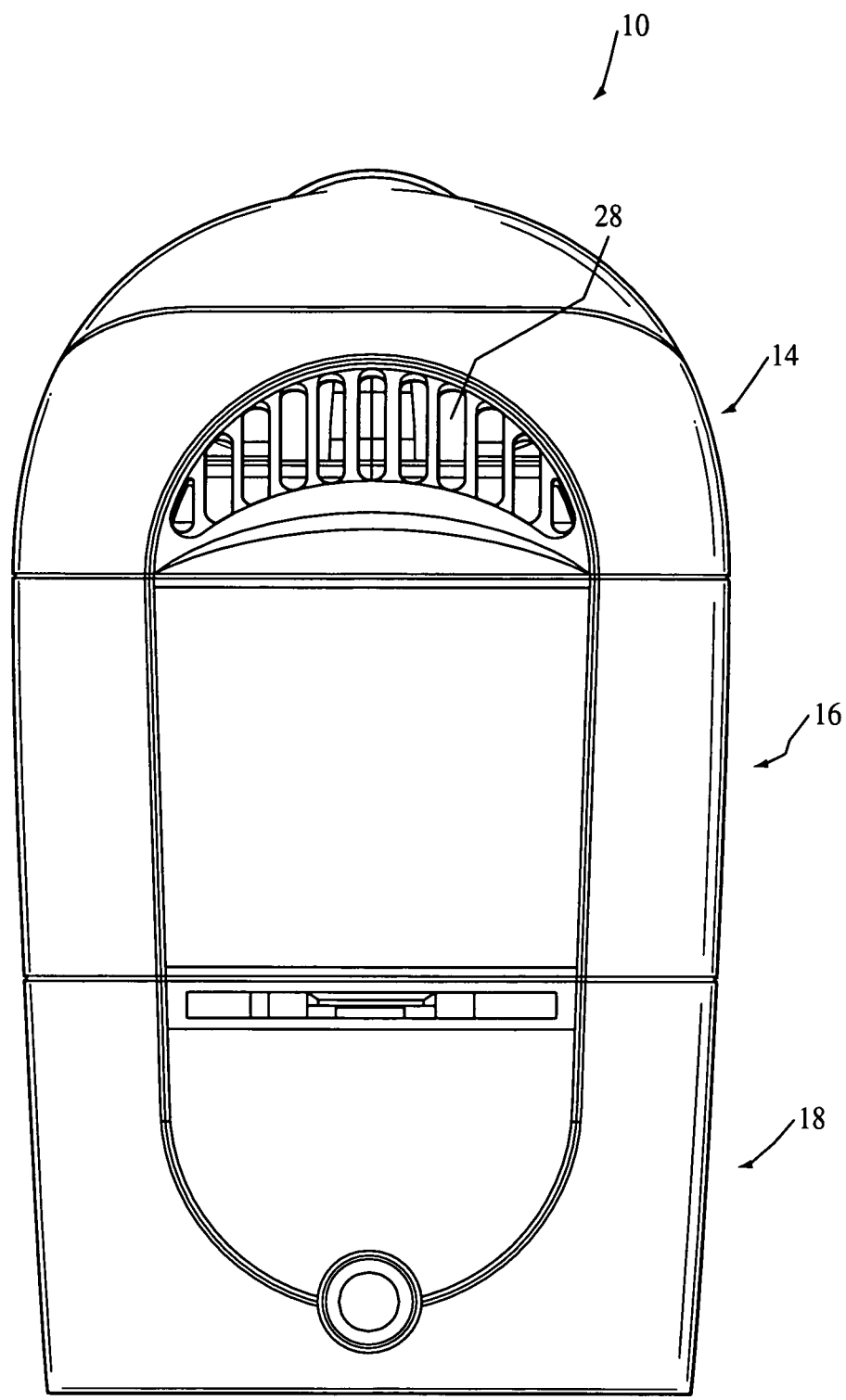
Figure 2:
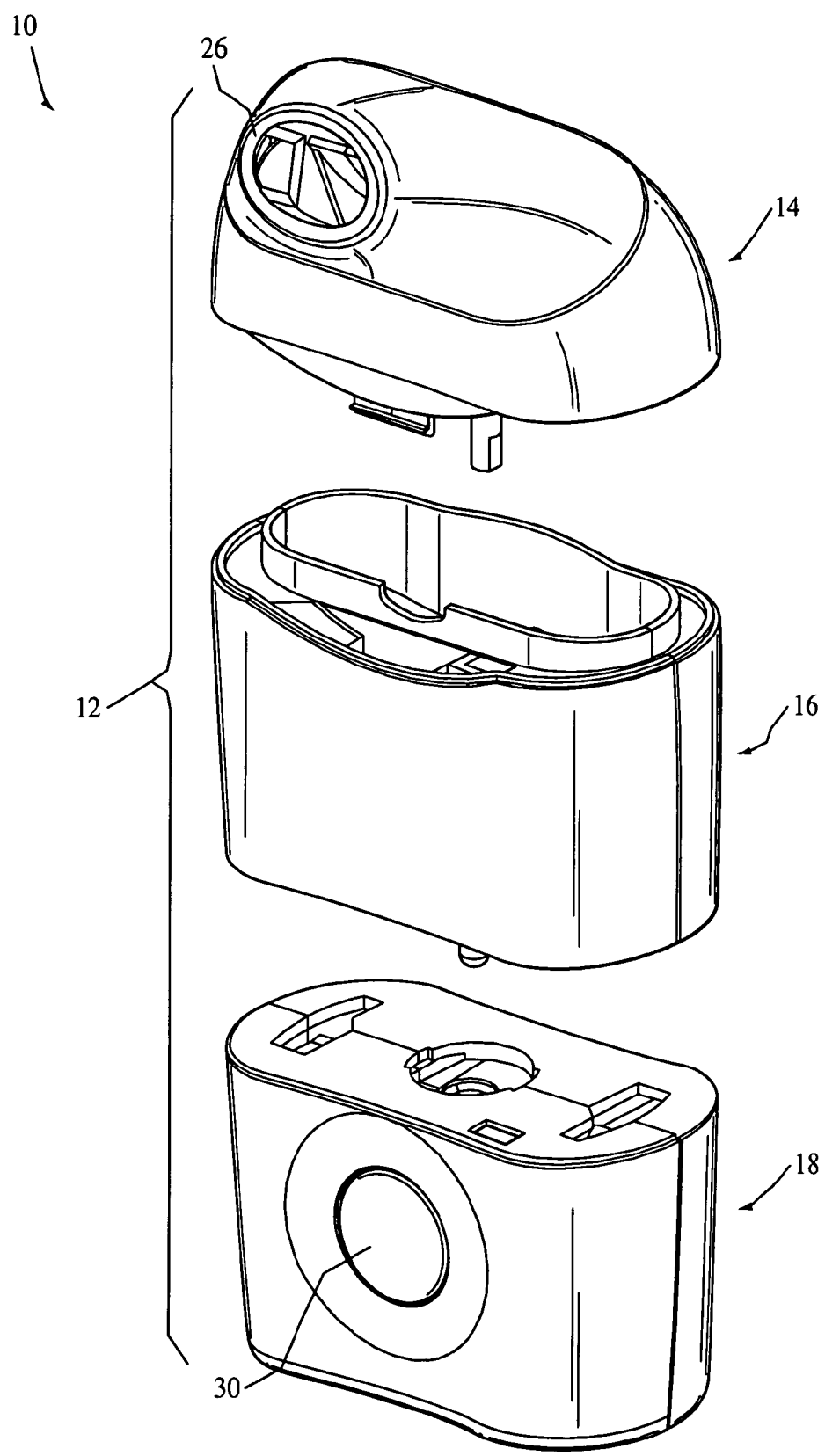
FIG. 2 is an exploded perspective view of the nebulizing device in accordance with an embodiment of the invention.

FIG. 1A is a perspective view, FIG. 1B is a front elevational view, and FIG. 1C is a rear elevational view of an exemplary illustration of a handheld nebulizing device 10 according to an embodiment of the invention. The device 10 as illustrated includes a housing 12. While the housing 12 of the present invention can be a unitary structure, in one embodiment, and as illustrated, the housing is formed from three modules, including a mouthpiece module 14, a intermediate module 16, and a base module 18 that can be coupled and decoupled from one another. As shown most clearly in the exploded perspective view of FIG. 2, the housing 12 comprises a mouthpiece housing portion 20 for the mouthpiece module 14, a intermediate housing portion 22 for the intermediate module 16, and a base housing portion 24 for the base module 18.

As will be described in greater detail below, the mouthpiece module 14 generally functions to deliver nebulized drug solution particles to a user through an outlet port 26. Atmospheric air is drawn into the housing 12 through an air inlet port 28 formed on the rear of the mouthpiece housing 20, as seen in FIG. 1C. Prior to delivery of the nebulized drug solution particles, the mouthpiece module has internal structure that separates larger drug solution droplets from the nebulized particles that are delivered to the user and returns such larger droplets to a drug solution pool or reservoir, as will be described.

The intermediate module 16 generally functions to contain a pool or reservoir of drug solution to be delivered to a user. The pool of drug solution includes a metered dose of the drug solution provided by the user to device 10. Intermediate module 16 also carries an aerosol generator that nebulizes the drug solution for delivery to the user.

The base module generally contains the device electronics and has a control interface 30, such as a manually operable button to enable the user to activate the device 10.

Figure 3:
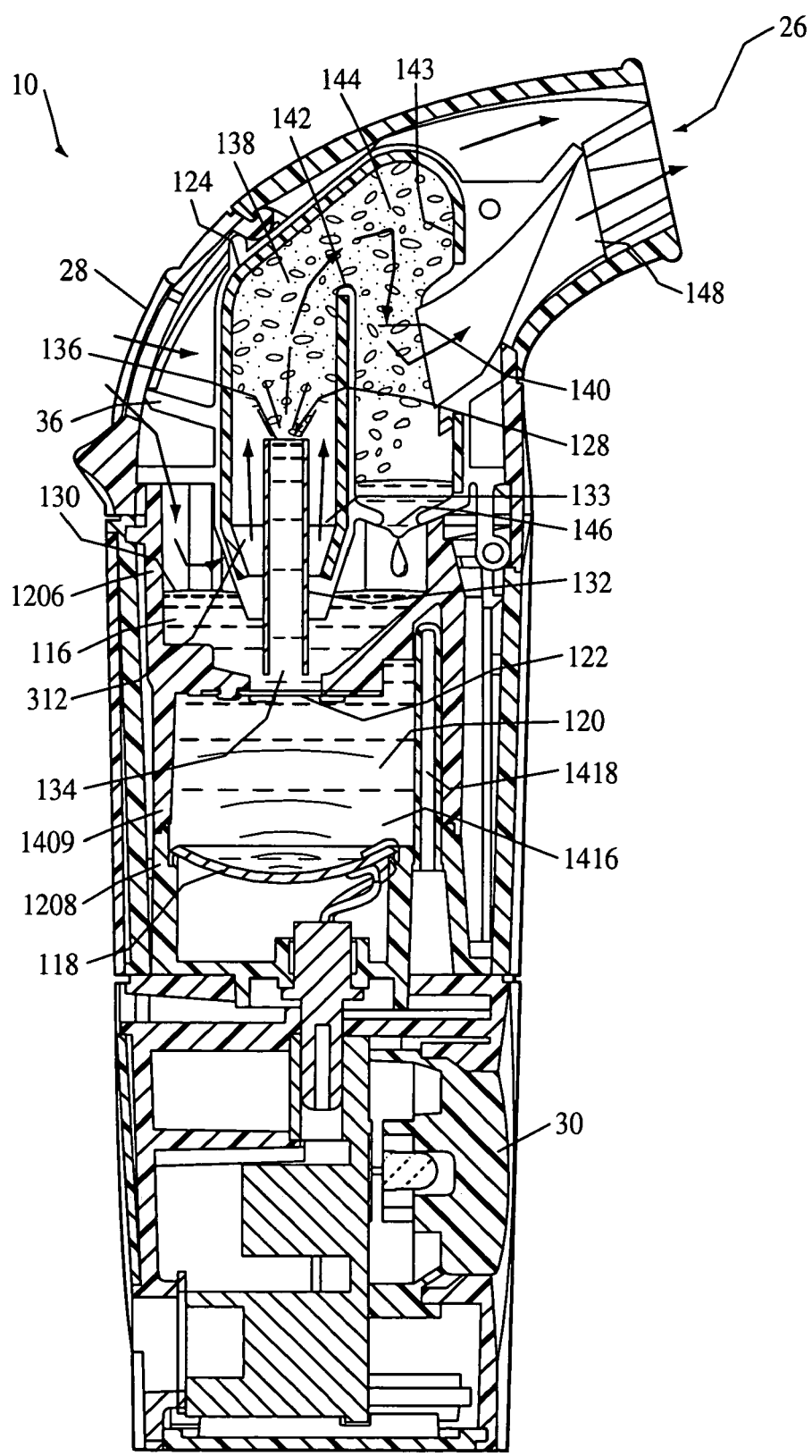
FIG. 3 is a cross-sectional view of the nebulizing device shown in FIG. 1B, taken along section line 3-3, according to one embodiment of the invention.

As illustrated in the cross-section of FIG. 3, the nebulized particles of the drug solution are formed in the device 10 from drug solution 116 that sits upon aerosol generator 118. Many different types of aerosol generators are known and may be used in certain embodiments of the invention. In one embodiment, and as illustrated, the aerosol generator 118 comprises an aerosol generator that generates acoustic waves within the drug solution 116. More specifically, the acoustic waves are transmitted from aerosol generator 118 to drug solution 116 via a fluid 120 between the drug solution 116 and aerosol generator 118. The drug solution is sealed from the fluid 120 by a thin barrier 122, which permits acoustic waves to pass therethrough and be transmitted from fluid 120 to drug solution 116.

In the embodiment illustrated in FIG. 3, the aerosol generator 118 comprises a concave piezoelectric transducer with a silver electrode. The piezoelectric transducer 118 generates acoustic waves at a generator frequency, such as, in a non-limiting example, 2.5 MHz. The acoustic waves are focused by the concave configuration of the piezoelectric transducer 118 at a focal point that is at a focal length from aerosol generator 118. Device 10 is arranged such that the focal point is within drug solution 116, adjacent to or at the bottom of a guide tube 132, as will be described.

In one embodiment, fluid 120 may primarily be comprised of water. In some instances, a sterilant, such as alcohol, or another sterilant, may be added to the fluid 120.

The aerosol generator may have additional or alternate structural and functional characteristics as described in International Application No. PCT/AU2003/001079 (International Publication Number WO 2004/017848), hereby incorporated by reference in its entirety. This invention also contemplates that any other aerosol generator present in the art could be used with the unique aspects of the present invention. For instance, the device may also be a traditional planar ultrasonic nebulizer, a vibrating mesh nebulizer, a vibrating plate nebulizer, or an electrospray nebulizer.

The drug solution present at the focal point of the acoustic waves will absorb the ultrasonic energy from drug solution 116. That is, the focused acoustic waves will generate a focused stream of drug solution, which the stream begins at a point that can also be considered the beginning of the fountain. Towards the top of the stream or fountain 128, the fountain sheds particles to aerosolize the drug solution. Some of the drug solution in the fountain 128 may not be nebulized, but rather form larger droplets of the drug solution that will be returned to the drug solution 116 as described later.

In some embodiments of the invention, the nebulization of the drug solution at fountain 128 may be enhanced when the focal point of the acoustic waves coincides (exactly or substantially) with a surface 130 of the drug solution in drug solution 116. In such embodiments, the level of surface 130 may be controlled with some particularity to enhance the operation of fountain 128.

According to some embodiments of the invention, and as previously mentioned, a guide tube 132 may be disposed within drug solution 116 such that a first end 134 (the lower end in the figures) of guide tube 132 may be positioned proximate to barrier 122, and a second end 136 of guide tube 132 may extend out of drug solution 116. In such instances, a portion of the drug solution may be urged into the guide tube at the first end 134 resulting in the fountain 128 being formed at the second end 136. The portion of the drug solution 116 within guide tube 132 is propelled toward second end 136 of guide tube 132 by the ultrasonic energy from the acoustic waves. At second end 136 of guide tube 132, the energized drug solution stream exits the guide tube 132.

Continuing with reference to FIG. 3, nebulized particles pass through device 10, from drug solution 116 to outlet port 26, via a separator structure 124, to the outlet 26. Separator structure 124 includes a first region 138 and a second region 140. Second end 136 of guide tube 132 extends into first region 138, and first region 138 receives particles of the drug solution therefrom. Second region 140 is in immediate communication with outlet port 26. A wall 142 is formed in separator structure 124 between first region 138 and second region 140. The drug solution is communicated between first region 138 and second region 140 via a passage 144 above wall 142. The various components of separator structure 124 may be arranged such that the nebulized particles may pass through to outlet port 26, while the larger droplets of the drug solution may, due to size and/or weight, contact surfaces of separator structure 124, such as separator wall 142 or far wall 143 and condense on the contacted surface. The drug solution that condenses on separator structure 124 in second region 140 will be returned to drug solution 116 via a drug solution return 146. Drug solution return 146 may be disposed at a lower end of second region 140. The drug solution that condenses on separator structure surfaces in the first region 138 will return to the drug solution 116 through a passage between an exterior surface of the guide tube 132 and surrounding walls of the separator structure 142.

As described above and as illustrated in the figures (e.g., FIGS. 1C and 3), the housing 12 of device 10 includes an inlet port 28. At inlet port 28, intake gas is received by device 10. A delivery flow path may be established between inlet port 28 and the housing outlet port 26 that directs at least a portion of the intake gas such that the intake gas motivates nebulized particles from fountain 128, through separator structure 124, to outlet port 26.

Referring again to FIG. 3, intake gas directed into separator structure 124 via separator inlet 312 may flow past guide tube 132, through passage 144, and out of housing 12 at outlet port 26. The nebulized particles formed at fountain 128 may be motivated by the flow of the intake gas along the delivery flow path as the intake gas passes fountain 128 and proceeds toward outlet port 26. In an alternate embodiment, the intake gas may be provided by a self-contained gas source rather than by atmospheric air.

In some embodiments of the invention, activation of aerosol generator 118 may generate sufficient energy to enable aerosol particles of the drug solution to be propelled by fountain 128 into separator structure 124, and out the outlet 26. As particles are propelled by fountain 128 into separator structure 124, the atmosphere within separator structure 124 may be disturbed such that air present at separator inlet 312 may be drawn up into separator structure 124. That is, the movement of fountain 128 may create a negative pressure within the housing 12, in a region between the housing inlet port 28 and the separator inlet 312, and a positive pressure in the separator structure 124 above the fountain 128. Pulling air into separator structure 124 via separator inlet 312 may initiate the flow of intake gas along a delivery flow path, which will motivate the nebulized particles formed at the fountain 128 toward outlet port 26. Thus, the atmospheric disturbances caused by the nebulized particles from fountain 128 and the resulting flow of intake gas along the delivery flow may function in a cooperative manner to "drive" nebulized particles from fountain 128 to the user without requiring additional moving parts such as fans, compressors, or the like. Of course, such devices could be used to further increase the flow rate of nebulized drug should such a result is deemed desirable. As described later, a one-way valve, may optionally be disposed in the delivery flow path, at a position between the inlet and outlet. Such valve would close to prevent gas that may be inadvertently exhaled by a user through the outlet from being expelled to atmosphere through the air intake 28, but be normally open to allow nebulized particles to pass therethrough to the outlet for user visibility. It has been found that user's of nebulizers take comfort in seeing the nebulized drug being exhausted from the mouthpiece. This way they know that the device is working properly and that their medication is being delivered thereby enhancing patient satisfaction and compliance. Use of a one-way valve that is normally open permits a portion of the particles to be visually expelled from the mouthpiece.

FIGS. 8, 9A-9D, and 10 are exemplary illustrations of the base module 18 according to an embodiment of the invention. Base module 18 includes a user control interface 30 and control electronics 1010 contained in the base module housing 24.

Control interface 30 enables the user to interact with control electronics 1010 to control device 10. In addition to providing a housing for control electronics 1010 and control interface 30, the base module housing 24 includes a intermediate module interface 812 that enables base module 18 to be selectively coupled to intermediate module 16, as will be described later.

According to various embodiments of the invention, control interface 30 enables the user to control various aspects of the operation of device 10. Control interface 30 may include a knob, a button, a switch, a keypad, or other controls.

Alternatively, the device could be controlled by an external memory encoded with instructions or wirelessly via an RF or Infrared signal. In a non-limiting example, control interface 30 may include a power button 814 that may be depressed by the user. In one embodiment, the power button 814 may be formed from silicon, or other materials such that power button may resiliently move inwardly when depressed by the user, and return to its original configuration when released such as an elastomeric membrane switch. Power button 814 activates and de-activates the aerosol generator 118.

Figure 10:
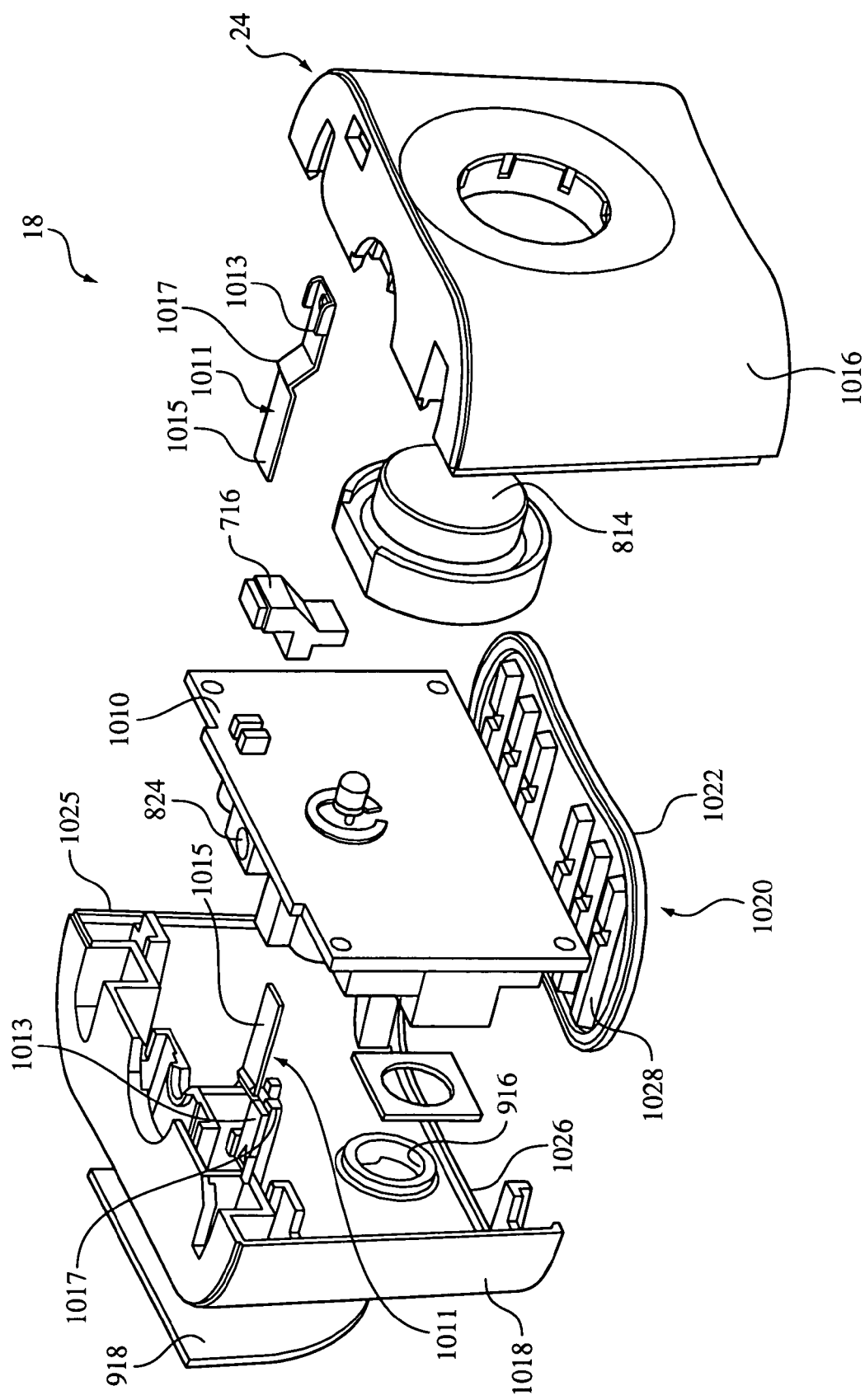
FIG. 10 is an exploded perspective view of the base module of the drug delivery device, according to one embodiment of the invention.

Referring to FIG. 10, control electronics 1010 are housed inside of base module housing 24. Control electronics 1010 may control various aspects of operation of device 10. Control electronics 1010 may include, for instance, hardware, software, firmware, or other electronics. Control electronics 1010 may include a power interface 916 that enables power to be delivered from a power source to device 10. The power source may include an AC source, such as a wall outlet or other AC sources, or a DC source, such as one or more batteries, or other DC sources. In some embodiments, an internal power source may be provided within base module housing 24.

Figure 8:
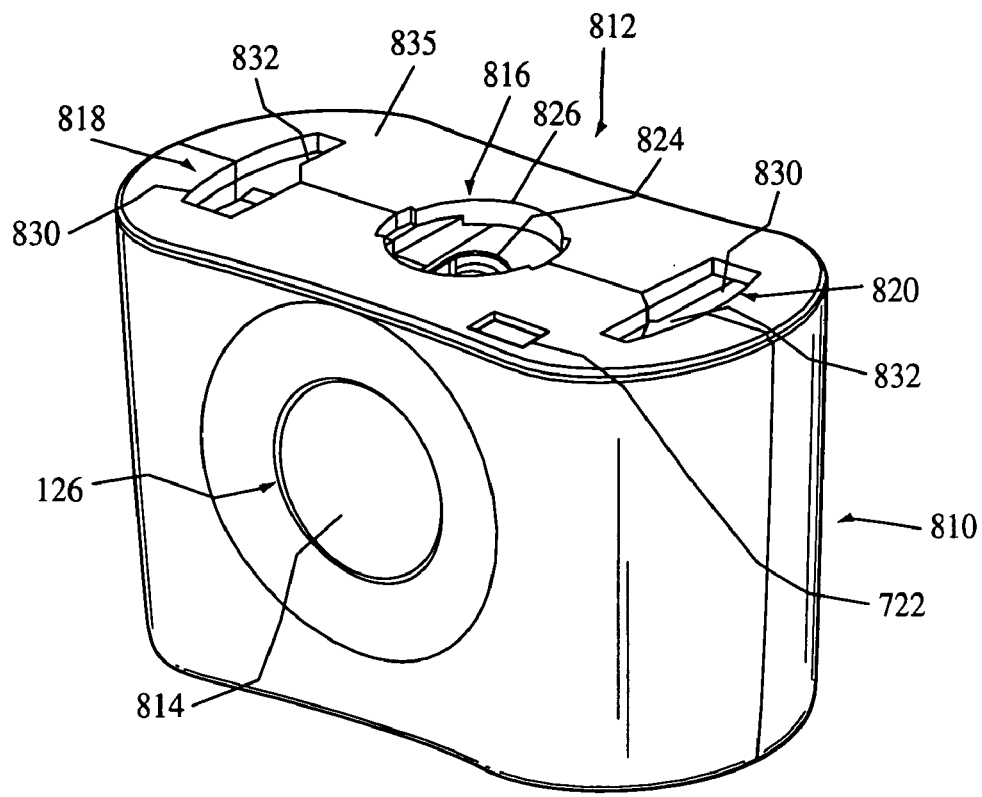
FIG. 8 illustrates a perspective view of an embodiment of the base module of the drug delivery device.
Figure 9A:
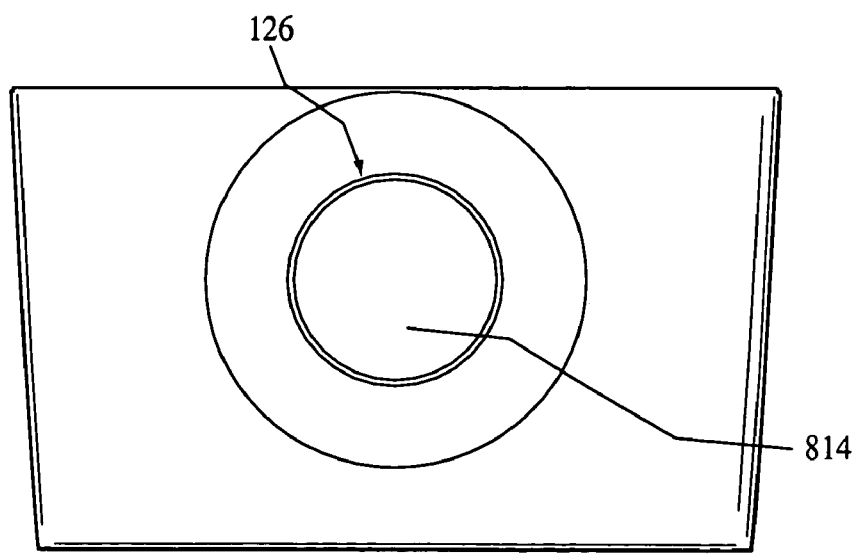
FIGS. 9A-9C illustrate front, back, and top elevation views of an embodiment of the base module of the drug delivery device.
Figure 9B:
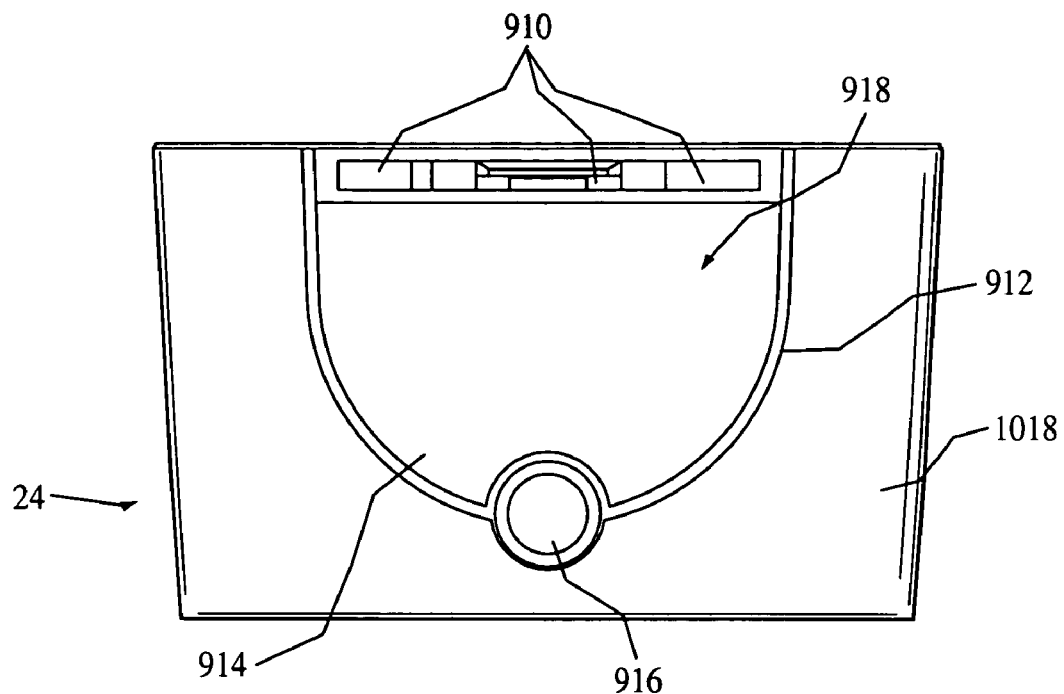
Figure 9C:
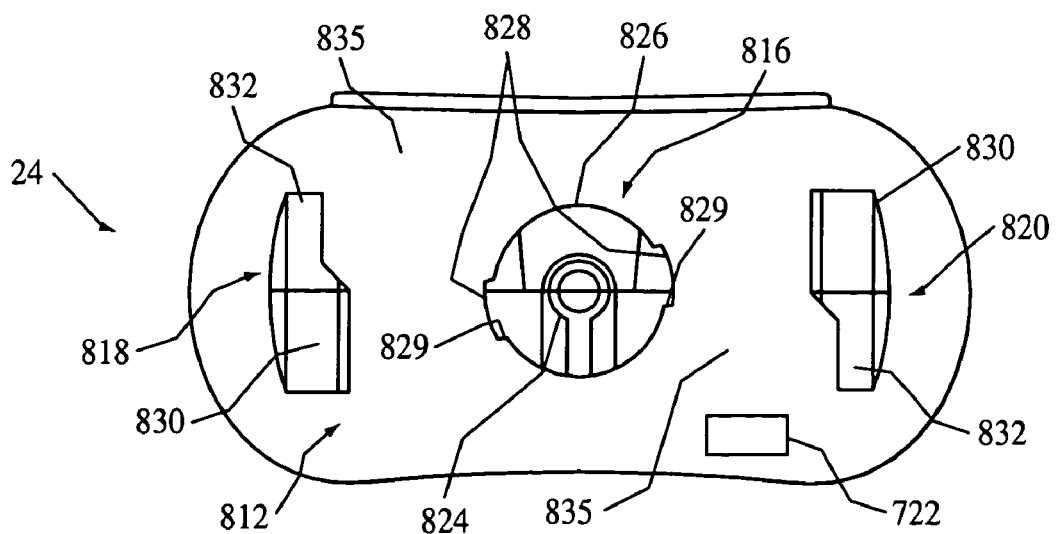

As shown in FIGS. 8 and 9C, the base module 18 has an intermediate module interface 812 that interfaces with a base module interface 1112 of intermediate module 16 (see FIGS. 11B and 11C) to selectively couple base module 18 with intermediate module 16. Intermediate module interface 812 includes a collar interface opening 816, a first slot 818, a second slot 820, and portion of a cup/base light pipe interface 722, as will be described later. As will also be described, and as shown in the figures, base module interface 1112 forms the other portion of the cup/base light pipe interface 722.

The intermediate module interface 812 includes a metal electrical connector receiver 824 and a collar receiver opening 826 formed in the upper surface 835 of the base module 18. Electrical connector receiver 824 is electrically connected with the control electronics 1010 and is connected to an electrical connector 1130 associated with the aerosol generator 118 in the intermediate module 16.

Figure 11A:
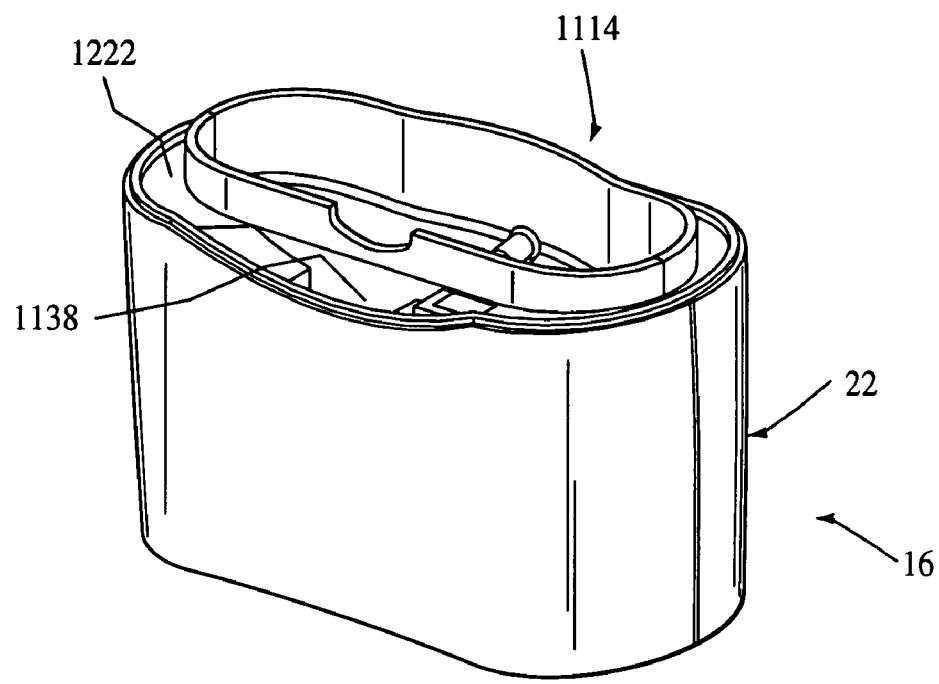
FIGS. 11A-11E are a perspective view and front, back, top, and bottom elevation views of an embodiment of the intermediate module of the drug delivery device.
Figure 11B:
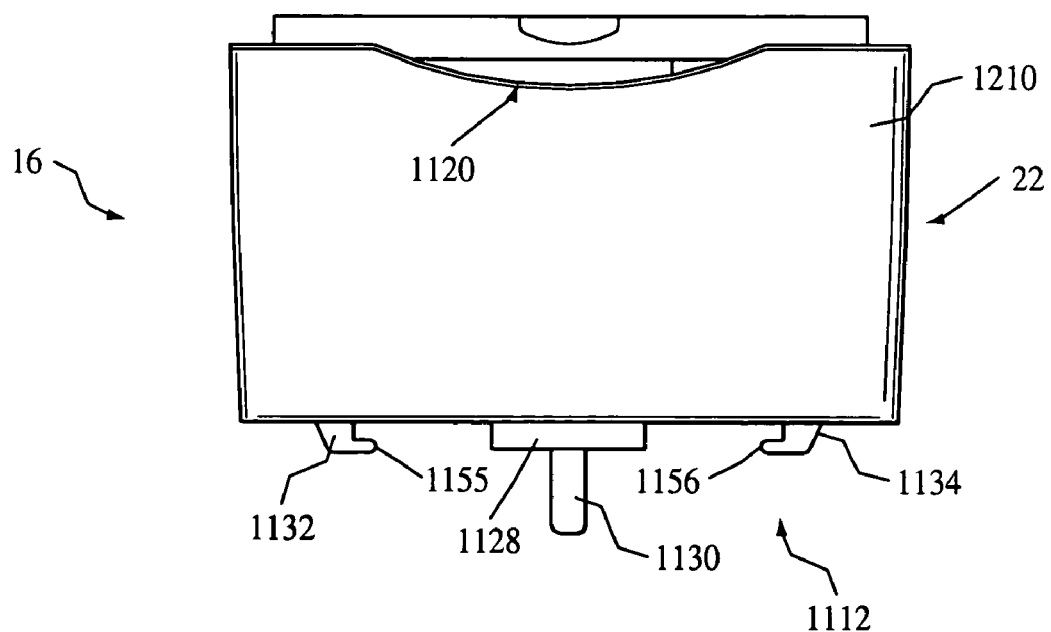
Figure 11C:
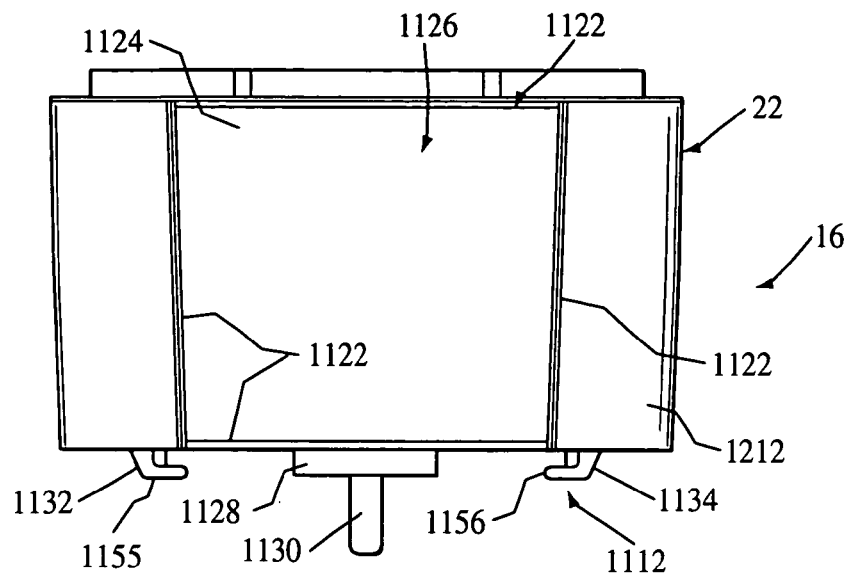
Figure 11D:
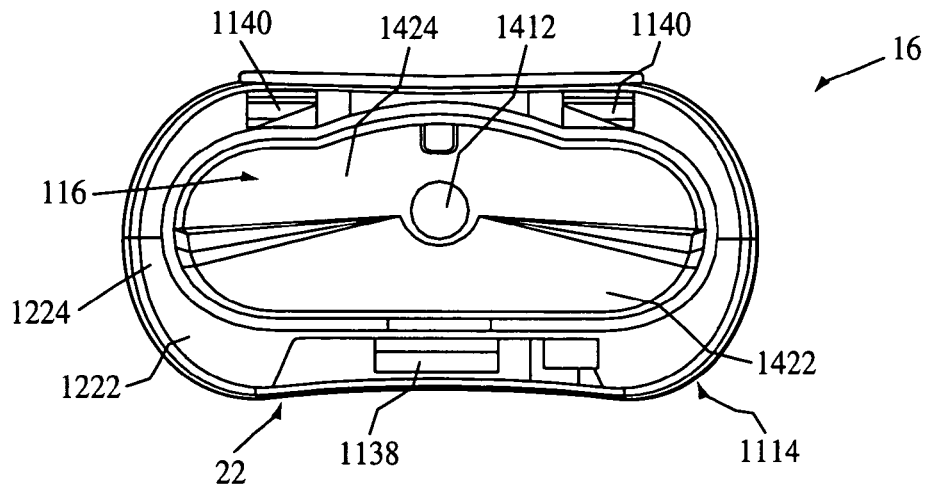
Figure 11E:
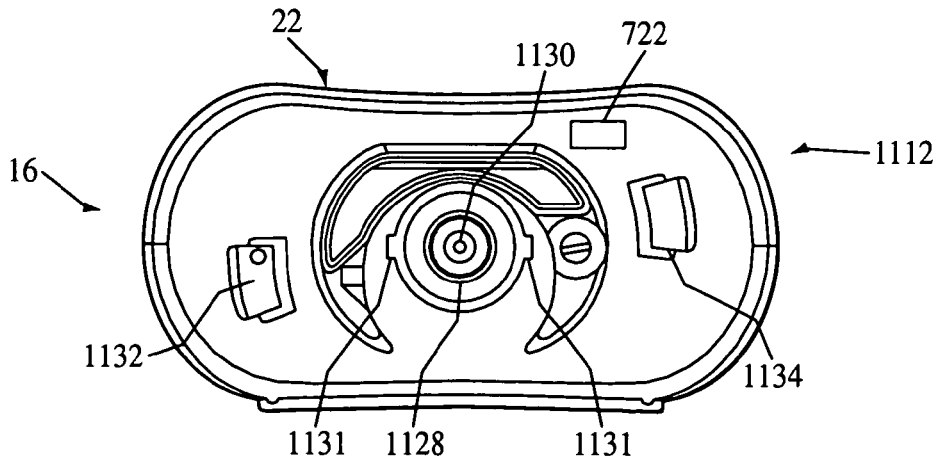

As shown in FIGS. 9C and 11E, collar receiver 826 receives a collar 1128 associated with intermediate module 16. More specifically, collar receiver opening 826 has a pair of enlarged opening portions 828, which are arranged to receive ridges 1131 provided on the collar 1128. Due to the enlarged profile of the collar 1128 at the ridges 1131, the collar 1128 can only be inserted into, or rotated within, collar receiver 826 when the ridges 1131 are positioned within enlarged portions 828. In addition, the end surfaces 829 at each end of the enlarged opening portions 828 serve as stop surfaces that may engage with the ridges 1131 when the ridges are received in the opening portions 828 to limit relative rotation between the base module 18 and intermediate module 16 when they are coupled to one another.

The first slot 818 and second slot 820 in the intermediate module interface 812 of base module housing 24 may include a first slot region 830 and a second slot region 832, the second slot region 832 being smaller in width than first slot region 830.

First slot 818 and second slot 820 are adapted to receive tabbed protrusions 1132 and 1134 (see FIGS. 11B and 11C) associated with intermediate module 16 such that the tab ends 1155, 1156 included on the tabbed protrusions 1132, 1134, respectively, are first received into first slot regions 830, while the ridges 1131 are aligned and inserted into the enlarged portions 828. Subsequently, the intermediate module housing 22 may be rotated with respect to the base or control module housing, so that the tabbed protrusions 1132, 1134 are slid to the narrower slot regions 832. As the tabbed protrusions 1132, 1134 on the intermediate module housing 22 are slid toward narrower slot regions 832 (e.g., moved clockwise as viewed in FIG. 9C into narrower regions 832), inwardly projecting tab ends 1155, 1156 associated with the tabbed protrusions are positioned underneath the upper wall region 835 of base module housing 24, so as to couple and secure the base module housing 24 with the intermediate module housing 22. Subsequent rotation in a relative opposition direction can then decouple the base module housing 24 from the intermediate module housing 22.

In some instances, as illustrated in FIG. 10, a leaf spring 1011 may be provided within each of first slot 818 and second slot 820. Leaf springs 1011 may provide a bias to the tabbed protrusions to hold intermediate module 16 and base module 18 in the engaged position.

More particularly, leaf springs 1011 are provided at a floor of each of first slot 818 and second slot 820 such that each of the leaf springs 1011 form a first slot region floor 1013 within first slot region 830 and a second slot region floor 1015 within second slot region 832, separated by a leaf spring ridge 1017. As is shown in FIG. 10, first slot region floor 1013 provides a deeper floor surface than second slot region floor 1015 within first slot 818 and second slot 820. Thus, as tabbed protrusions 1132 and 1134 are introduced into first slot regions 830, the tabbed protrusions 1132 and 1134 do not substantially contact first slot region floor 1013. However, as intermediate module 16 and base module 18 are rotated with respect to each other to position tabbed protrusions 1132 and 1134 into second slot regions 830, tabbed protrusions 1132 and 1134 contact leaf spring ridges 1017 such that inwardly projecting tab ends 1155 and 1156 are biased upwards into upper wall region 835, effectively inhibiting further rotation. By applying sufficient force to overcome this bias applied by leaf spring ridges 1017, tabbed protrusions 1132 and 1134 can be moved past leaf spring ridges 1017 and into second slot regions 830. When tabbed protrusions 1132 and 1134 are positioned in second slot regions 830, second slot region floors 1015, which are shallower that first slot region floors 1013, contact inwardly projecting tab ends 1155 and 1156 to provide a bias to tab ends 1155 and 1156 into upper wall region 835 that is not as strong as the bias provided by leaf spring ridges 1017. In this position, leaf spring ridges 1017 act as retaining walls that secure tabbed protrusions 1132 and 1134 in second slot regions 830.

Base module housing 24 houses various components of base module 18. In one embodiment, as illustrated in FIG. 10, base module housing 24 is formed from a first base clamshell member 1016, a second base clamshell member 1018, and a base member 1020. Base member 1020 includes a peripheral projecting tab 1022, while first base clamshell member 1016 and second base clamshell member 1018 each include, towards lower edges thereof, a base member receiving groove 1026 (not shown on clamshell member 1016). Second base clamshell member 1018 also includes a pair of base clamshell grooves 1025 along opposite side edges thereof, while first base clamshell member 1016 includes a pair of base clamshell tabs 1024 along opposite side edges thereof. Base module housing 24 may be formed by joining first base clamshell member 1016, second base clamshell member 1018, and base member 1020 such that base member tab 1022 fits into base member grooves 1026, and base clamshell tabs 1024 fit into base clamshell grooves 1025. First base clamshell member 1016, second base clamshell member 1018, and base member 1020 may be joined via one or more of a weld, an adhesive, a snap-fit, or other mechanisms for securing separate members to each other. In one embodiment, the base module housing portions are all molded from ABS material.

In some embodiments of the invention, as shown in FIG. 9B, the exterior of second base clamshell member 1018 may include one or more vents 910, a base grip section defining arcuate ridge 912, a base grip section 914, and a power source opening 916. Vents 910 enable atmospheric air outside of base module housing 24 to be communicated to various components within base module housing 24, such as control electronics 1010, for example, for cooling thereof. The arcuate ridge 912 defines base grip section 914. A separate base grip member 918 may be fixed to base grip section 914 of the molded base module housing 24. Base grip member 918 may be composed of a resilient or rubber-containing material to enhance a user's grip of base module 18. The grip 918 may be overmolded onto the plastic (e.g., ABS housing) shell 1018, for example, at region 914. In other embodiments, the base grip member 918 may be separately formed and later adhered to or otherwise affixed to the housing shell 1018.

The base member 1020 of the base or control module housing 24 may also include one or more vents 1028. The vents 1028 enable atmospheric air outside of base module housing 24 to be communicated to various components within base module housing 24, such as control electronics 1010, for example. The vents 1028 and 910 provide for cooling of the base module electronics 1010.

FIGS. 11A-11E, 12, 13, and 14 are exemplary illustrations of intermediate module 16 according to an embodiment of the invention. Intermediate module 16 includes the intermediate module housing 22, base module interface 1112, a mouthpiece module interface 1114, a drug solution pool container 1206, and an aerosol generator housing 1208 that carries the previously described acoustic wave generator 118. In some embodiments, aerosol generator housing 1208 and/or drug solution pool container 1206 are molded from polycarbonate or ABS, or a combination thereof.

Figure 12:
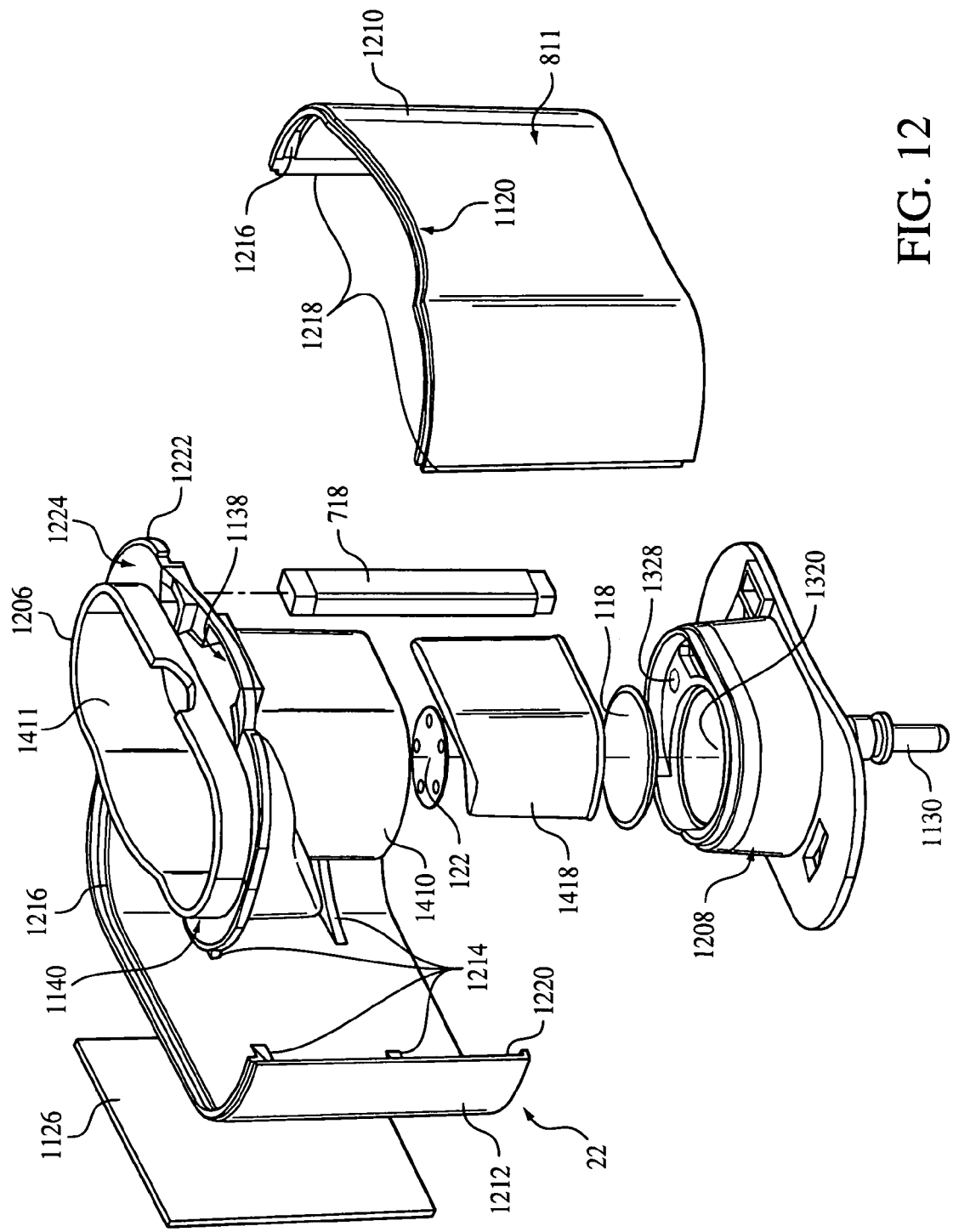
FIG. 12 is an exploded perspective view of the intermediate module of the drug delivery device, in accordance with one embodiment of the invention.

In an embodiment of the invention, as shown in FIG. 12, intermediate module housing 22 may include a first cup clamshell member 1210, and a second cup clamshell member 1212. Intermediate module housing 22 houses various components of device 10 disposed in intermediate module 16. First cup clamshell member 1210 and second cup clamshell member 1212 may include a plurality of clamshell support members 1214. Clamshell support members 1214 provide structural support to first cup clamshell member 1210 and second cup clamshell member 1212.

In one embodiment, intermediate module housing 22 may be formed by joining first cup clamshell member 1210 and second cup clamshell member 1212 around drug solution pool container 1206 and aerosol generator housing 1208. First cup clamshell member 1210 and second cup clamshell member 1212 both have an upper edge defining an elongated curved groove 1216. First cup clamshell member 1210 has vertically extending elongated tabs 1218 along opposite ends thereof. Second cup clamshell member 1212 has vertically extending elongated grooves 1220 along opposite ends thereof. Drug solution pool container 1206 includes a peripheral, radially outwardly extending flange 1222. First cup clamshell member 1210 may be joined with second cup clamshell member 1212 around drug solution pool container 1206 and aerosol generator housing 1208 by inserting cup clamshell member tabs 1218 into cup clamshell member grooves 1220, and outwardly extending flange 1222 has a peripheral edge that is received into drug solution pool housing grooves 1216. First cup clamshell housing portion 1210 and second cup clamshell member 1212 may be joined around drug solution pool container 1206 and aerosol generator housing 1208 via a weld, an adhesive, a snap-fit, or other mechanisms for securing separate members to each other. In one embodiment, the composition of intermediate module housing 22 may be ABS.

As shown in FIG. 11C, second cup clamshell housing portion 1212 may include a plurality of projecting ridges 1122 formed in a square or alternatively shaped configuration defining a cup grip section 1124. A cup grip member 1126 may be adhered, overmolded, or otherwise fixed to cup grip section 1124. Cup grip member 1126 may be composed of a tacky or resilient material to enhance a user's grip of intermediate module 16.

Figure 13:
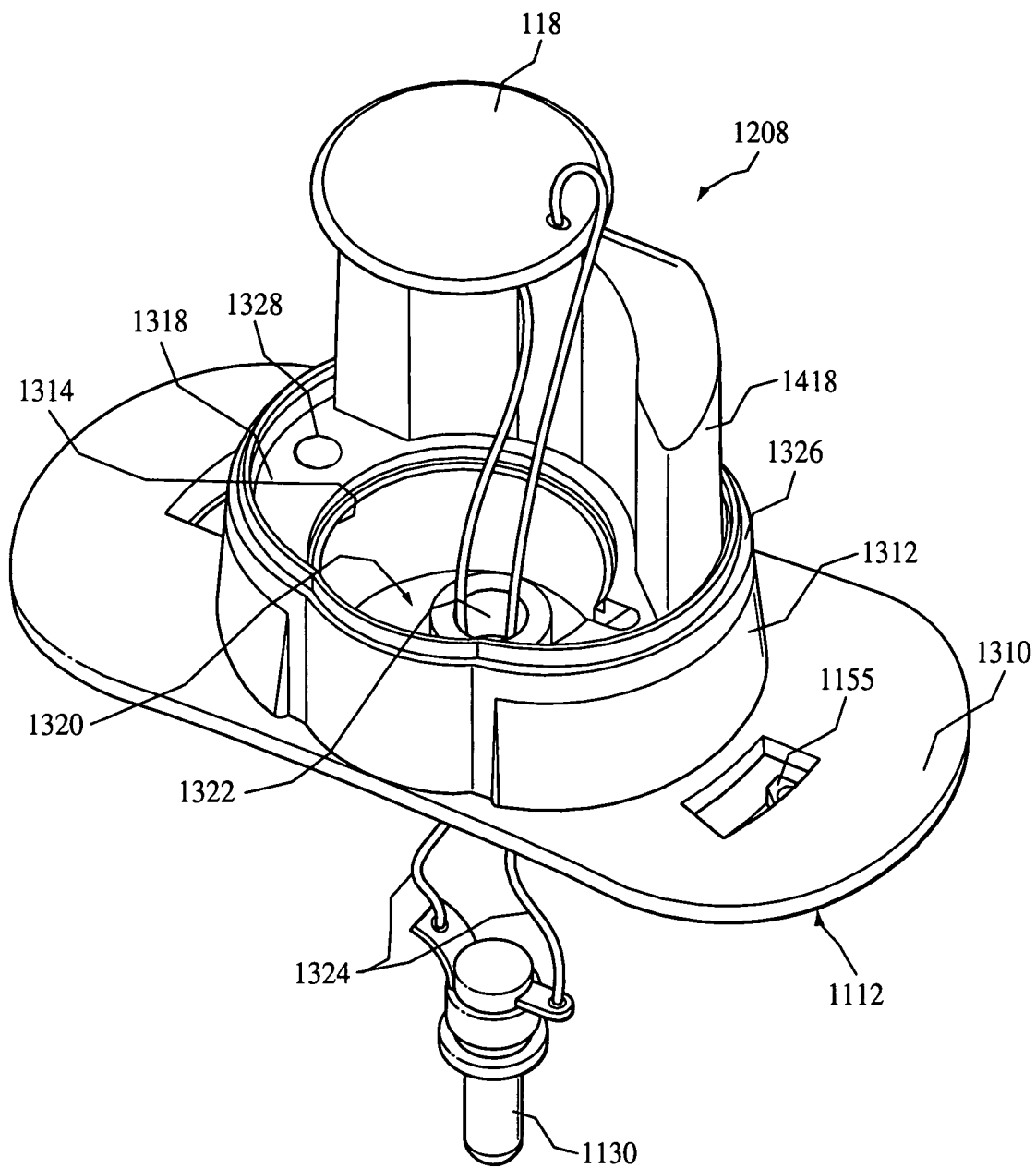
FIG. 13 is a perspective view of an aerosol generator housing of the intermediate module of the drug delivery device, in accordance with an embodiment of the invention.

As can be appreciated from FIGS. 11B, 11C, and 13, the base module interface 1112 of the intermediate module 16 enables intermediate module 16 to be selectively coupled to base module 18 via intermediate module interface 812 of the base module. The base module interface 1112, including tab extensions 1155, 1156, may be formed as an integrally molded structure with aerosol generator housing 1208. Base module interface 1112 mounts the previously mentioned electrical connector 1130 that is connected with connector 824 of the electronics 1010 carried within base module 18.

As shown best in FIG. 13, aerosol generator housing 1208 may include a flange portion 1310 that provides on its lower side the base module interface 1112. The aerosol generator housing 1208 may further include a pedestal portion 1312, an aerosol generator seating portion 1314, and a fluid filler opening 1328. Pedestal portion 1312 extends upwardly from the flange portion 1310. At an upper surface 1318 of pedestal portion 1312, aerosol generator seating portion 1314 is provided for seating the aerosol generator 118. The aerosol generator 118 is peripherally sealed to the seating portion 1314 so that fluid 120 within the fluid chamber (as will be described) and sitting on the aerosol generator 118 does not leak into cavity 1320 formed between the aerosol generator 118 and aerosol generator housing 1208. Cavity 1320 has a connector opening 1322 that receives the electrical connector 1130 that enables power and/or control signals to be transmitted to aerosol generator 118 from control electronics 1010.

Figure 14:
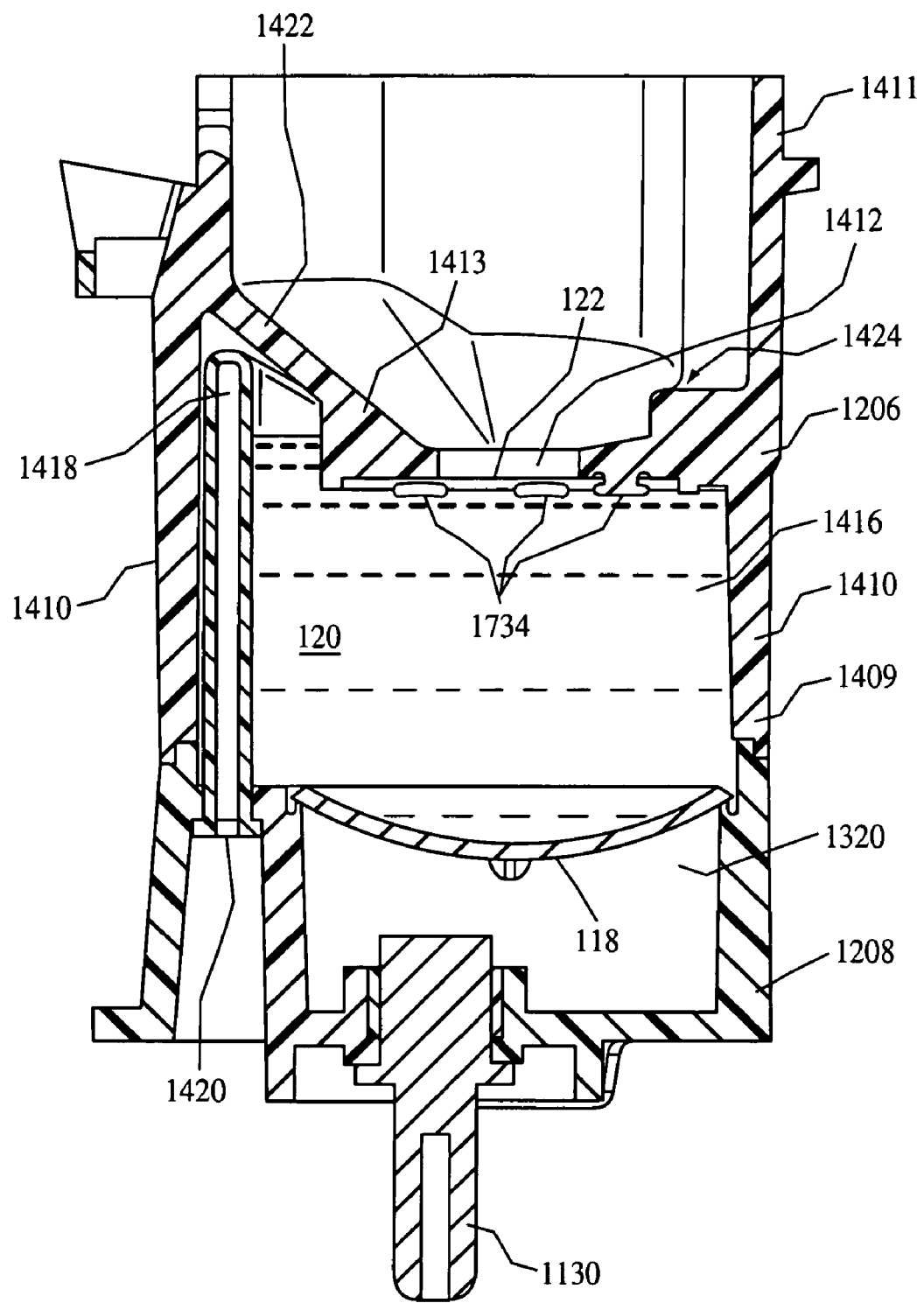
FIG. 14 is a cross-sectional view of one embodiment of the aerosol generator housing and a drug solution pool container of the intermediate module of the drug delivery device.

As best seen in FIG. 14, the aerosol drug solution pool container 1206 has a lower skirt portion 1409 that cooperates with the aerosol generator housing 1208 and aerosol generator to define a sealed chamber 1416 for containing fluid 120. The pool container 1206 further includes an upper cup region 1411 for containing the drug solution 116. The cup region 1411 is separated from the chamber 1416 by a separating wall 1413. The separating wall 1413 has an opening 1412 formed therethrough. The opening 1412 is sealed by the previously described barrier 122, which is disposed between the fluid 120 and drug solution 116. Drug solution pool container 1206 may be joined with aerosol generator housing 1208 by having the lower skirt 1409 secured to an outer edge 1326 of pedestal portion 1312 via a weld, an adhesive, or other mechanisms for securing one component to another.

Fluid 120 may be introduced into fluid chamber 1416 via chamber opening 1328 (see FIG. 13). Chamber opening 1328 is provided at upper surface 1318 of pedestal portion 1312, and may be accessible at a side of aerosol generator member 1208 opposite from fluid chamber 1416 (illustrated, for example, in FIG. 11E). Subsequent to the introduction of fluid 120 into fluid chamber 1416, chamber opening 1328 may be sealed by being plugged with a suitable material.

Figure 15:
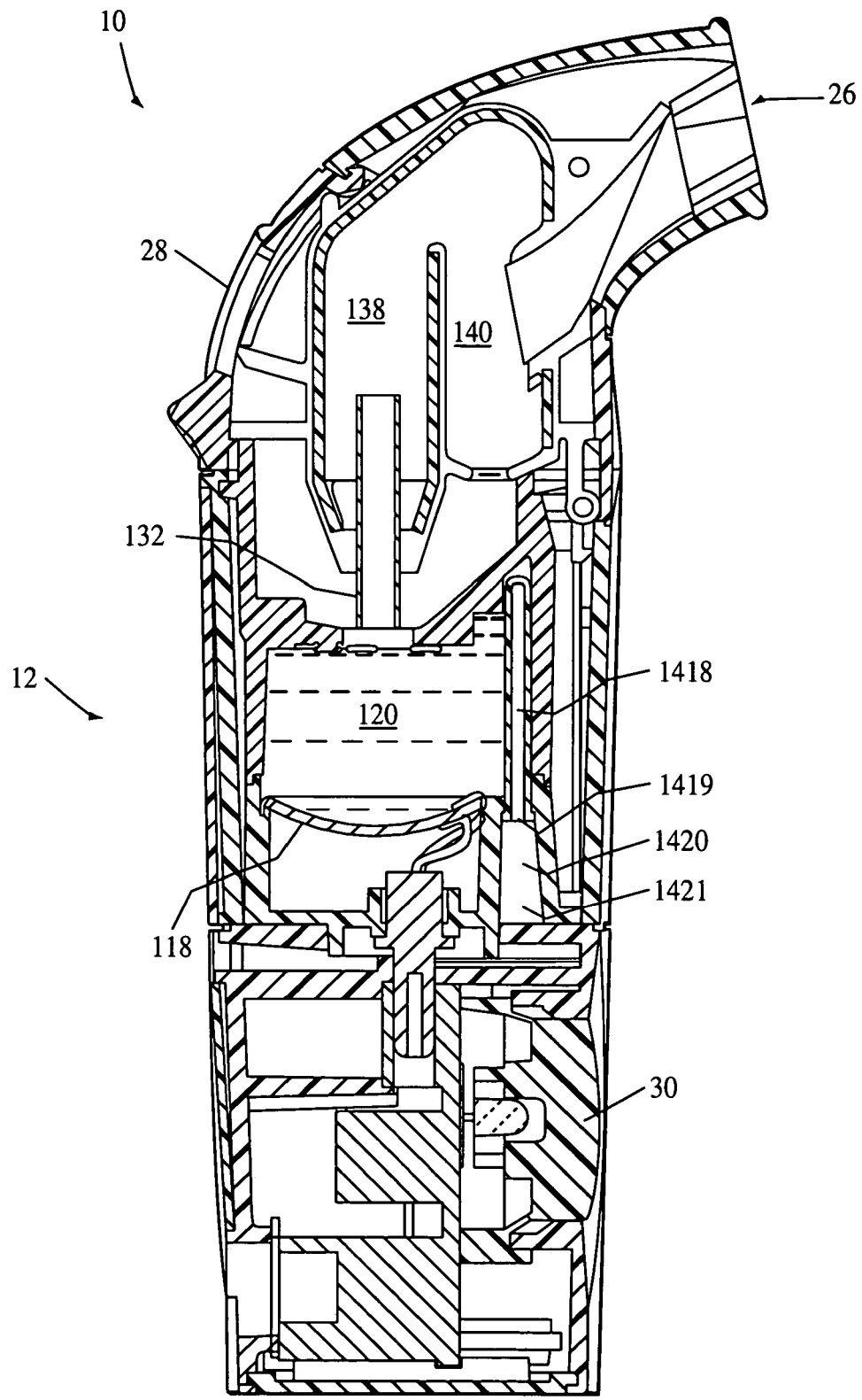
FIG. 15 is a cross-sectional view of the nebulizing device of FIG. 1B, taken along section line 15-15, according to an embodiment of the invention.
Figure 16:
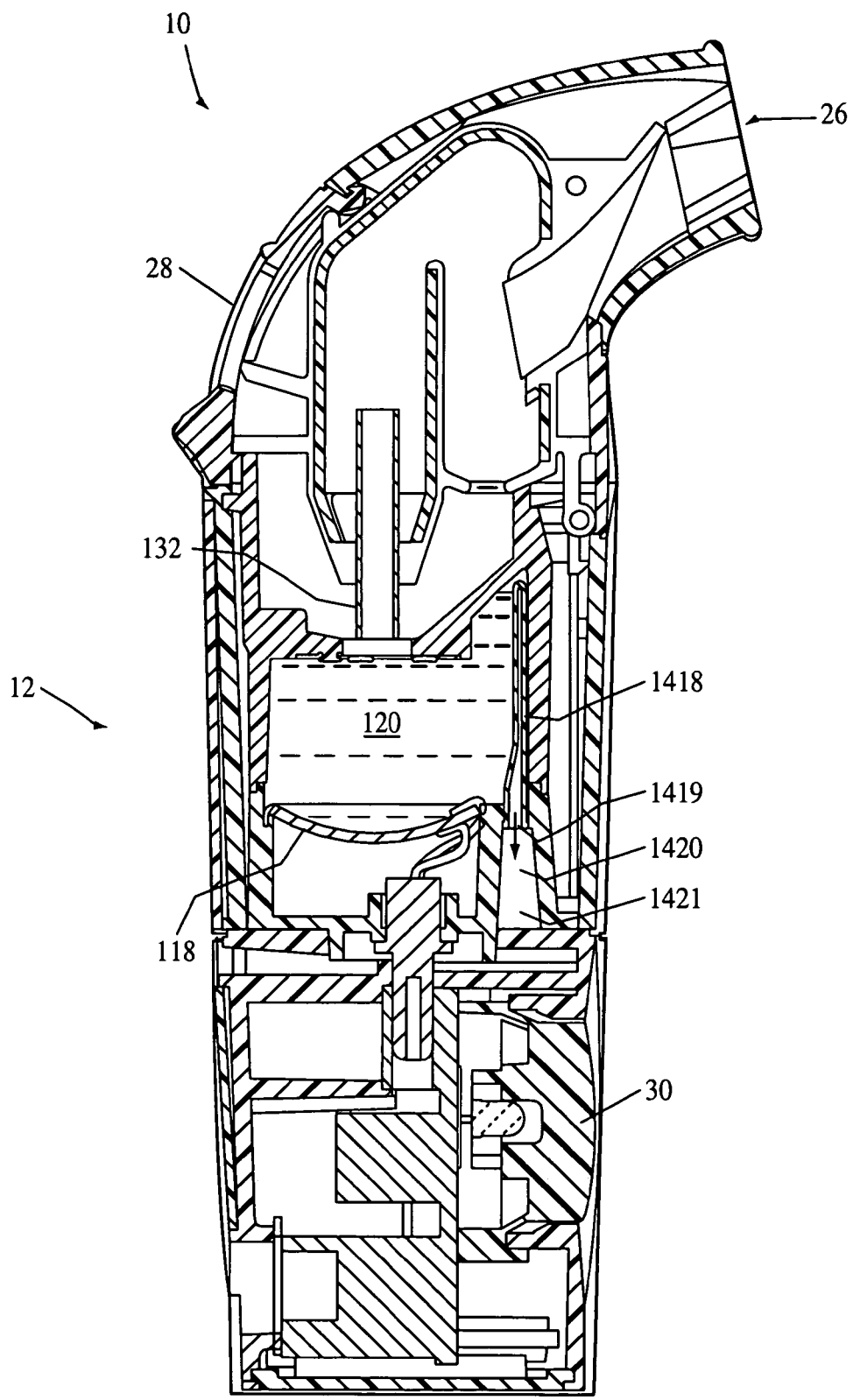
FIG. 16 is a cross-sectional view of the nebulizing device of FIG. 1B, taken along cross-section line 16-16 of FIG. 1B, according to an embodiment of the invention.

In one embodiment of the invention, as seen most clearly in FIGS. 13, 15 and 16, a structure 1418 is disposed within fluid chamber 1416 and is in contact with the fluid 120. This resilient structure may be reduced in volume so as to reduce the amount of space it occupies in the chamber 1416 when the volume of fluid 120 increases. In the embodiment illustrated, the structure 1418 comprises an expansion protection bladder composed of a deformable resilient material to accommodate expansions in the volume of fluid 120, and thereby protect other components from potential damage due to changes in the volume. For instance, aerosol generator 118, barrier 122, may potentially be subject to damage in the event that ambient temperature surrounding device 10 is low enough to cause a fluid temperature of fluid 120 to approach or reach freezing. Or, fluid 120 may also expand in the event that the temperature of fluid 120 rises. In the event of such expansion of fluid 120, the resilient structure will reduce in volume to accommodate the increased volume of the fluid. This, for example, may prevent cracking of the fluid chamber 1416.

FIGS. 15 and 16 are illustrations of how the structure 1418 operates according to one example. In FIG. 15, the fluid temperature of fluid 120 may be at or near normal room temperature. FIG. 16 illustrates how the expansion protection bladder may deform to accommodate an expansion of fluid 120. Expansion protection bladder is composed of a deformable material, such as, for instance, silicon, or other deformable materials. The bladder has an opening 1419 peripherally sealed to an opening in the upper surface 1318 of pedestal 1312. The opening 1419 leads into an internal space in the bladder that is exposed to atmospheric pressure. Structure 1418 may be vented to the atmosphere via a passage 1420 that leads to an open space 1421 in the housing. The space 1421 is not sealed and this is allowed to bleed air and receive air to and from the atmosphere. Because the amount of air displaced is small and only needs to be done over a long period of time, there is no need for a large vent in the intermediate module housing 22, as the slow permeation of air to and from region 1421 is sufficient.

It is contemplated that the structure 1418 can be formed from different materials, or from a plurality of different members. For example, the structure can be made from an elastomeric material, such as silicone or another elastomeric material, a sponge material, a closed cell foam material, or other materials. In another embodiment, the structure 1418 may include a rigid structure that is biased into the chamber 1416 by a spring (e.g., a coil spring or leaf spring) or other resilient member. The rigid structure would form a moving seal with the chamber 1416 and take up more or less of the chamber volume based on the fluid volume as described above. In this instance, the spring constant of the spring member would be tuned for optimal resistance. Where a bladder is employed, the spring constant is engineered with several variables in mind, such as the durometer and thickness of the bladder material.

In another contemplated embodiment, the structure comprises a resilient material part of the skirt wall 1409 of the chamber 1416. For example, the skirt wall 1416 may have a window formed therein, and a thin sheet of resilient material may cover and seal the window. Increasing volume of the fluid 120 in this embodiment would cause the resilient material to bulge outwardly.

The barrier 122 provided between fluid 120 and drug solution 116 may include a material that meets various design criteria. Design criteria may include, for example, a prescribed thickness, an elasticity, a durability at high temperatures, an acoustic wave transmission property, or other criteria. This construction enables acoustic waves to be transmitted through the barrier 122, from fluid 120 to drug solution 116.

As seen in FIG. 14, the barrier 122 is mounted over barrier opening 1412 by being mounted to barrier mounting surface 1414 formed on an underside of separating wall 1413.

Figure 17A:
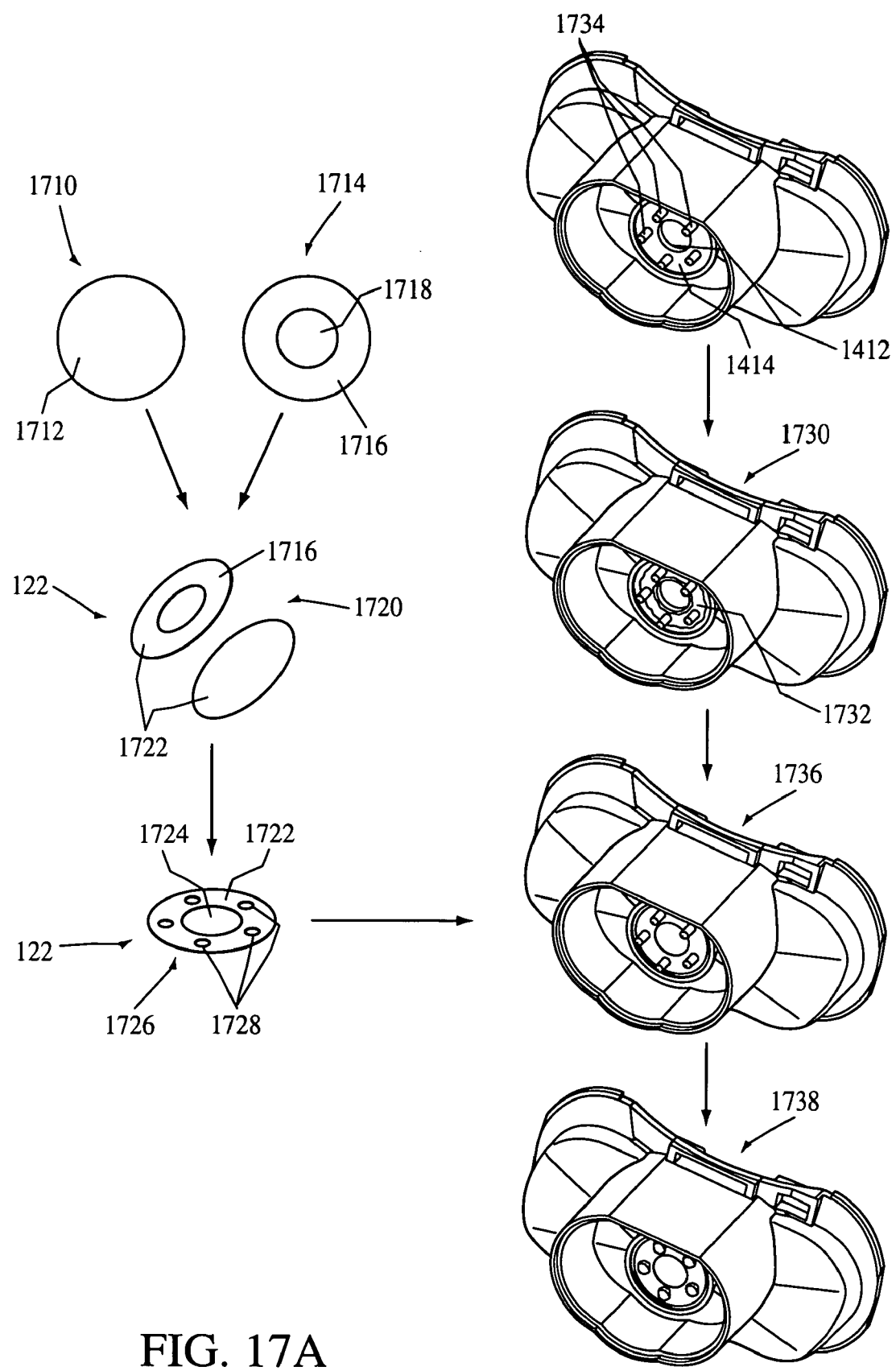
FIG. 17A is an illustration of one embodiment of a method of forming and mounting a barrier within the intermediate module of the drug delivery device of the invention.
Figure 17B:
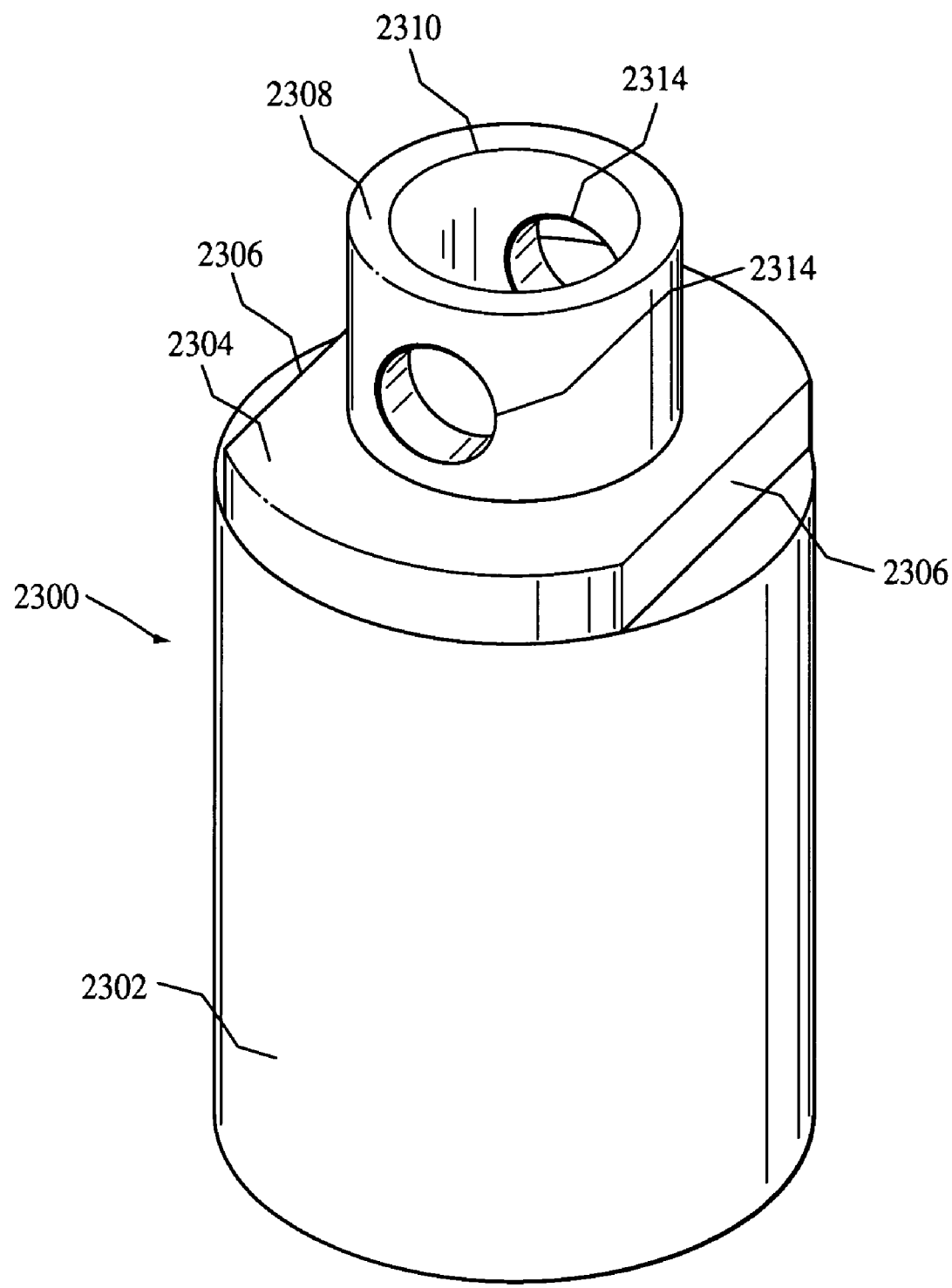
FIG. 17B is a perspective view of a mandrel in accordance with an embodiment of the invention.
Figure 17C:
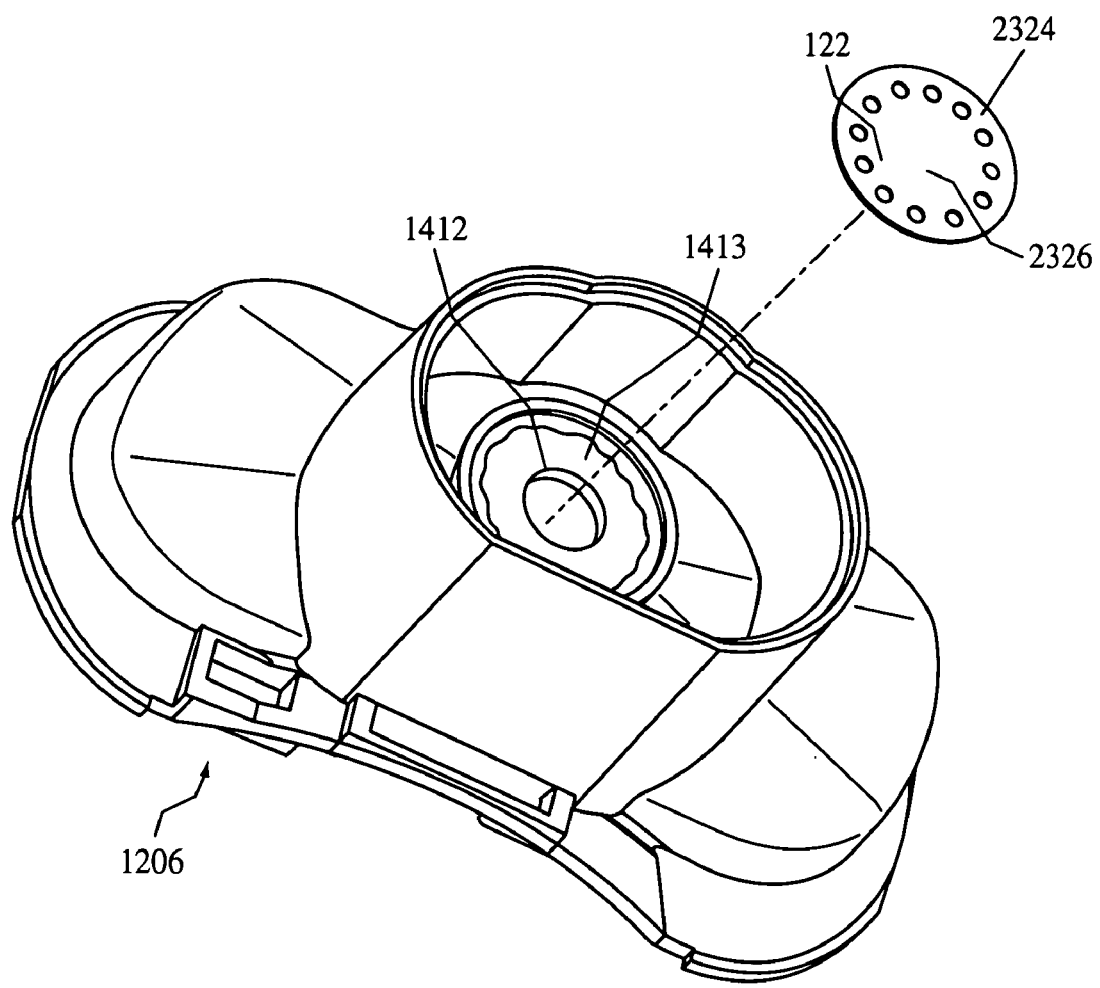
FIG. 17C is an exploded view of the drug solution container and barrier of an alternative embodiment of the invention.

FIG. 17A is an exemplary illustration of a method of forming and mounting barrier 122 according to an embodiment of the invention. At an operation 1710, a first barrier part 1712 is formed, for example, by being stamped from a roll of material. First barrier part 1712 may be stamped into a generally circular shape, or may be of another shape. First barrier part 1712 in one embodiment is of a thickness that is less than or equal to 0.0005 inches and greater than 0.0001 inches. First barrier part 1712 may be composed of polyetheretherketone (PEEK), or other similar materials.

At an operation 1714, a second barrier part 1716 is formed, again by being stamped from a sheet or roll of material. Second barrier part 1716 includes an opening 1718 generally defining a central portion of barrier 122. Second barrier part 1716 may be of a second barrier thickness greater than the first barrier thickness. For example, the second barrier thickness may be approximately ten times greater than the first barrier thickness. Second barrier part 1716 may be composed of polyetheretherketone (PEEK), or other materials.

The method includes an operation 1720, at which the first barrier part 1712 is sealed to second barrier part 1716 to form barrier 122. Second barrier part 1716 is sealed to first barrier part 1712 at a peripheral portion of first barrier part 1712 to form a peripheral portion 1722 of barrier 122. Peripheral portion 1722 defines a central portion 1724 (see operation 1726) of barrier 122 with a smaller thickness than a thickness of peripheral portion 1722. In a non-limiting example, first barrier part 1712 and second barrier part 1716 may be sealed via an ultrasonic weld, or otherwise sealed.

At an operation 1726, a plurality of holes 1728 are formed in the peripheral portion 1722 of barrier 122. In one embodiment, holes 1728 may be die cut in peripheral portion 1722 of barrier 122.

The method may include an operation 1730, in which barrier mounting surface 1414 of the drug solution container 1206 is coated with one or more sealants 1732. For example, barrier mounting surface 1414 may be coated with a silicon-based adhesive, or other sealants.

The mounting surface 1414 includes a plurality of integrally formed projections 1734. At an operation 1736, peripheral portion 1722 of barrier 122 is mounted to barrier mounting surface 1414. Mounting barrier 122 to barrier mounting surface 1414 positions central portion 1724 of barrier 122 over barrier opening 1412. At operation 1736, projections 1734 are received within holes 1728 of barrier 122.

At operation 1738, projections 1734 are deformed. Deforming projections 1734 functions to clamp peripheral portion 1722 of barrier 122 to barrier mounting surface 1414.

Because the barrier 122 has a substantially thicker peripheral portion than central portion, it can be more easily secured or clamped to the barrier mounting surface 1414 in comparison with a barrier that would have a periphery with the same thickness as the central portion. In addition, the thickness of the central portion of the barrier 122 can be engineered for optimal performance without concern that it may be too thin for optimal securement to the mounting surface 1414. In other words, in one embodiment of the present invention, the thickness of the central portion of the barrier 122 independent of the thickness of the peripheral portion enables each portion to have an optimized thickness to support its associated functionality.

In another embodiment, the first barrier part 1722 and the second barrier part 1716 are molded as a one-piece integral structure, with the peripheral part being of a greater thickness than the central part. The greater thickness of the peripheral part is better adapted for securement to the barrier mounting surface, while the thinner central part is better adapted for transmitting acoustic waves.

In yet another embodiment, barrier 122 is sealed to the drug solution container 1206 through use of a thermal staking process. This process may be utilized whether the barrier has a laminate construction formed from two or more barrier parts 1712, 1716 or molded together as a single one-piece structure.

A mandrel 2300 is then heated to a suitable temperature capable of melting at least a portion of at least one of the barrier 122 or separating wall 1413. As best appreciated with reference to FIGS. 17B-17E, the mandrel 2300 includes a fixture portion 2302 at one end adjacent a riser portion 2304. The riser portion provides bearing surfaces 2306 oriented to provide bearing surfaces for a wrench. The riser portion 2304 is also adjacent a cylindrical tube portion 2308 terminating at a surface 2312 having a hole 2310. The cylindrical tube portion 2308 has cross-drilled holes 2314.

Figure 17D:
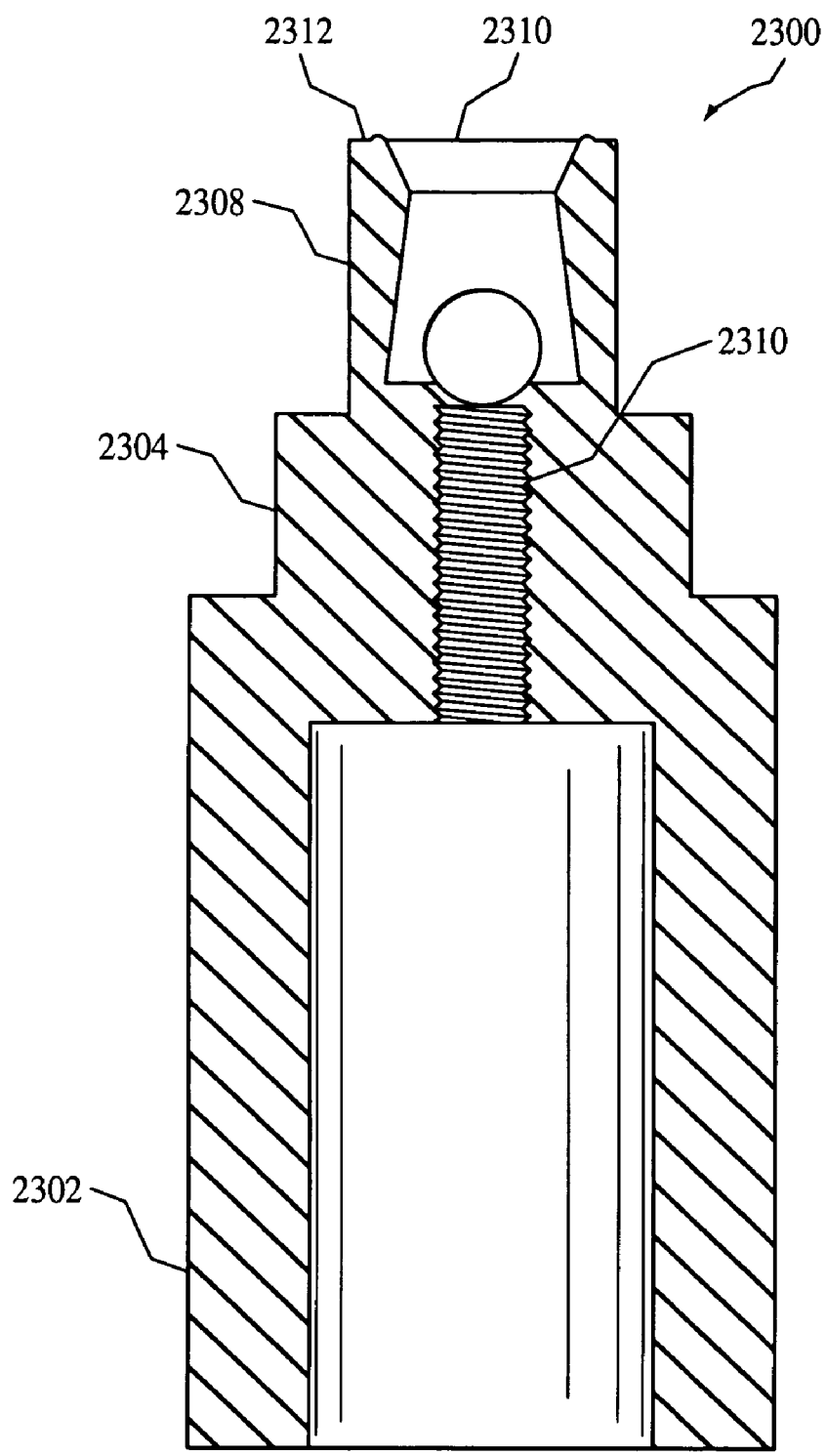
FIG. 17D is a cross-sectional view of the mandrel.
Figure 17E:
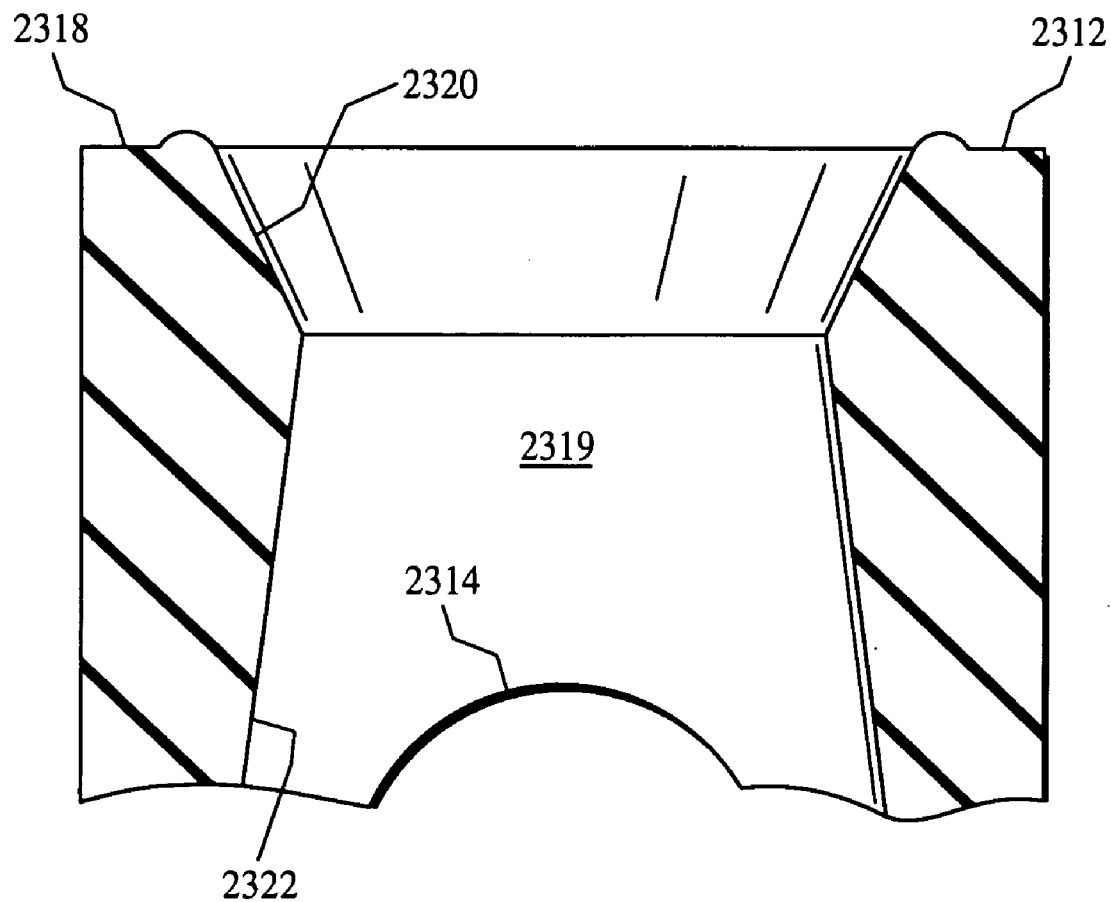
FIG. 17E is a partial cross-sectional view of the cylindrical tube of the mandrel.

The fixture portion is attached to a thermal press such as the 48H081TS manufactured by Dukane Corporation having a heater. As seen in FIGS. 17D and 17E, the mandrel has an internal threaded portion 2316 which is threaded onto a screw extending from the thermal press. When attached to the thermal press, the fixture portion operates to assist the threaded portion 2316 with maintaining alignment of the mandrel as well as insulate the heater. The inner surface 2319 of the cylindrical tube portion 2308 is defined by a tapered region 2320 and a tapered region 2322. Surface 2312 of the cylindrical tube portion 2308 includes an annular bead 2318 which is configured to contact a peripheral portion 2324 of barrier 122 during assembly to conduct heat to drug solution container 1206. The mandrel does not contact an interior portion 2326 of barrier 122. In combination, hole 2310 along with cross-drilled holes 2314 permit cooling air from the environment to pass into the interior of the mandrel in order to prevent the heat conducted by the mandrel from warping or otherwise damaging the interior portion 2326 of the barrier.

In use, the mandrel is used to thermally stake barrier 122 to drug solution container 1206. The thermal staking process includes selecting a material for the mounting surface 1414 of the separate wall 1413 and a material for barrier 122. The materials should have different melting temperatures. For instance, Polycarbonate having a melting temperature of approximately 300 degrees Fahrenheit may be chosen as the material drug solution container 1206, or at least for separating wall 1413 of the drug solution container 1206. Similarly, Polyetheretherketone having a melting temperature of approximately 700 degrees Fahrenheit may be chosen as the material for barrier 122. Of course a variety of other materials with different characteristics could also be utilized without departing from the scope of the present invention.

Next, barrier 122 and separating wall 1413 are sealed together by pressing bead 2318 against barrier 122. Bead 2318 conducts heat through barrier 122 into drug solution container 1206 to melt at least a portion of the separating wall while pressing barrier 122 to form a mounting surface 1414. With respect to the materials described above, the mandrel is heated to a temperature approximately between 300-700 degrees Fahrenheit. Barrier 122 remains substantially solid due to its higher melting point relative to the melting point of the mounting surface. The barrier/drug solution container assembly is then cooled to allow the mounting surface 1414 to sufficiently solidify (or cure). Of course, a similar effect could result by reversing the materials such that the barrier is melted rather than mounting surface 1414.

In one embodiment, the separating wall 1413 between the chamber 1416 and the cup region 1411 has an upper angled floor surface 1422 on which the drug solution 116 sits. The angled floor surface 1422 is essentially disposed one side of the opening 1412 formed in separating wall 1413. More specifically, an angled floor surface 1422 is disposed towards a same side of device 10 as outlet port 26. The floor surface 1422 on the opposite side of opening 1412 is essentially of a stepped configuration.

Opposite angled floor section 1422 and stepped floor section 1424 are shaped to drain toward barrier 122. The sloping configuration of floor surface 1422 is such that it continues to drain the drug solution 116 to the barrier 122 when the drug solution 116 is depleted and as the housing 12 may be tilted by a user during operation.

As best seen in FIGS. 11D, 11A and 12, mouthpiece module interface 1114 is provided by front slot 1138 and one or more rear slots 1140 formed in peripheral flange 1222 of the pool container 1206.

FIGS. 18A-18C and 19 are exemplary illustrations of the mouthpiece module 14 according to an embodiment of the invention. Nebulized particles of the drug solution held in intermediate module 16 may be communicated to the user via mouthpiece module 14. Mouthpiece module 14 includes a mouthpiece housing 20, an inner mouthpiece member 1912, and the guide tube 132. Guide tube 132 is securely held by inner mouthpiece member 1912, as described later, and the inner mouthpiece member 1912 is disposed inside of mouthpiece housing 20, as will also be described. The mouthpiece housing 20, in one embodiment, is molded from a polypropylene material, although other suitable materials can also be used. The guide tube 132, in one embodiment, is made from a corrosion resistant metal, such as stainless steel.

Figure 19A:
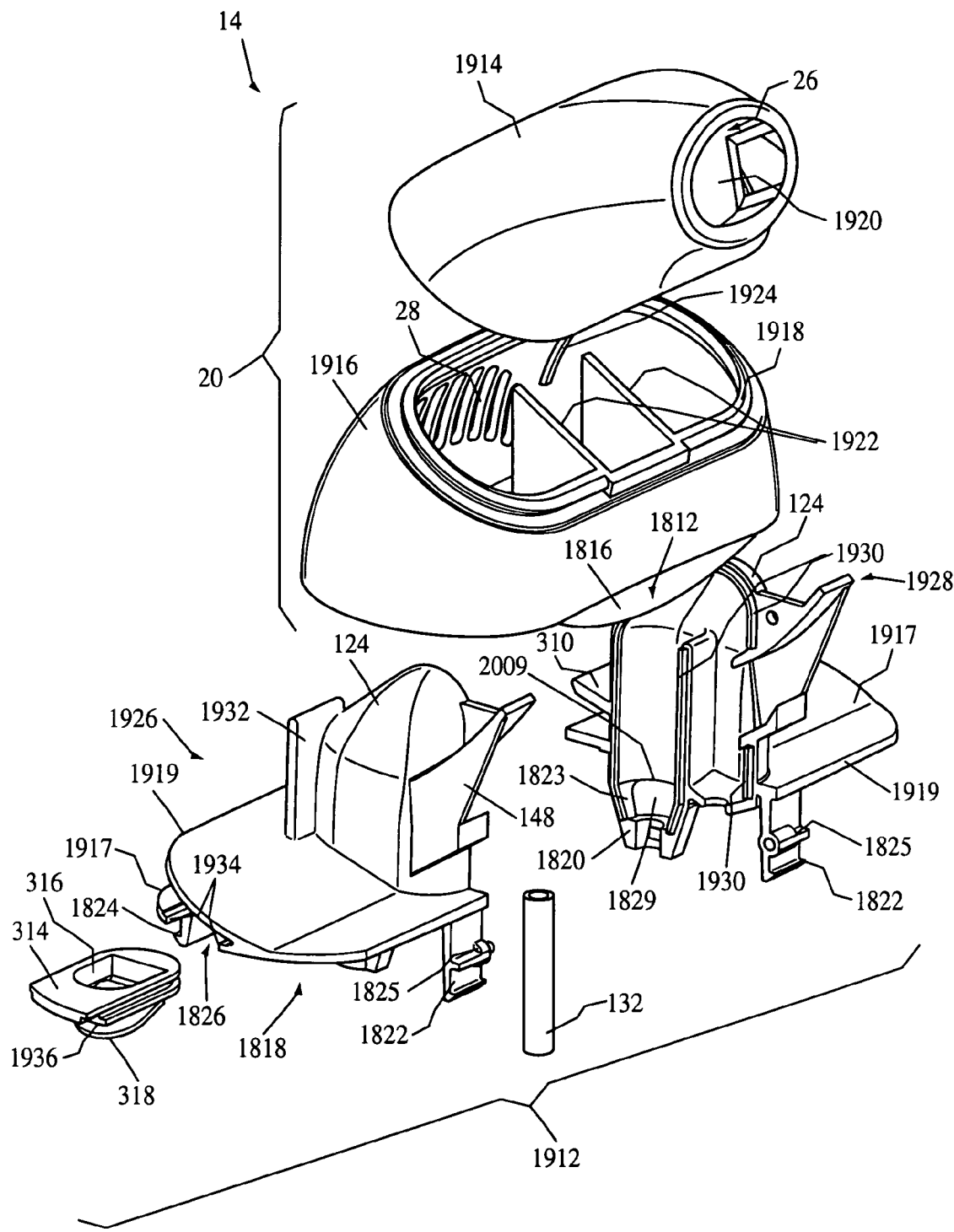
FIGS. 19A and 19B are exploded perspective views of the mouthpiece module of the drug delivery device according to one embodiment of the invention.
Figure 19B:
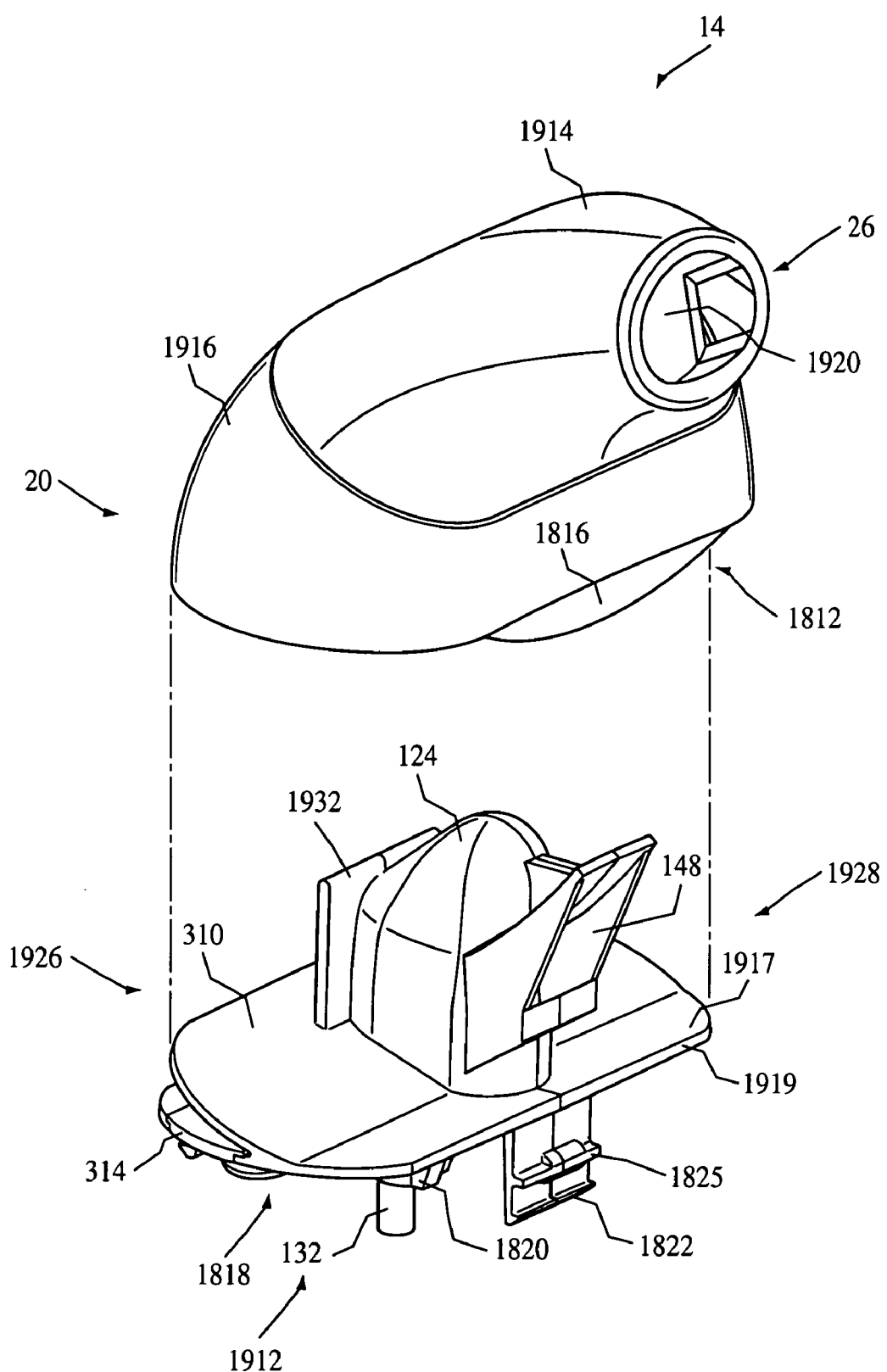

As shown in FIG. 19, mouthpiece housing 20 includes a first housing member 1914 and a second housing member 1916. Second housing member 1916 has an upper peripheral lip provided with a protruding ridge 1918. First housing member 1914 and second housing member 1916 may be joined such that mouthpiece housing ridge 1918 is received by one or more ridge receiving members (not shown) disposed at a peripheral lower edge of first housing member 1914. A mechanism for securing first housing member 1914 and second housing member 1916 to each other to form mouthpiece housing 20 may comprise a weld, an adhesive, a snap-fit between mouthpiece housing ridge 1918 and the ridge receiving members, or other mechanisms for securing components to each other.

The first housing member 1914 includes the outlet port 26. Outlet port 26 is disposed toward a side of device 10 to enable a user to position their mouth on mouthpiece housing 20 around outlet port 26 to receive the nebulized particles of the drug solution from device 10.

Figure 18A:
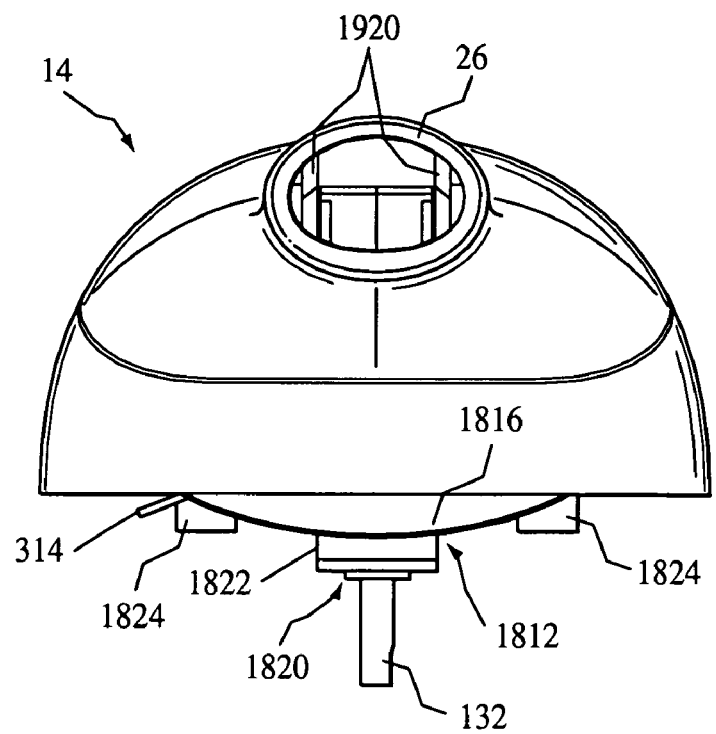
FIGS. 18A-18D are illustrations of front, side, and back plan views of one embodiment of a mouthpiece module of the drug delivery device of the invention.

As best seen in FIG. 18A, the first housing member 1914 includes a first pair of internal alignment ridges 1920. As best seen in FIG. 19, second housing member 1916 includes a second pair of alignment ridges 1922. When first housing member 1914 and second housing member 1916 are joined, the first pair of housing alignment ridges 1920 are aligned and functionally joined with the second pair of housing alignment ridges 1922 to form a channel into which inner mouthpiece member 1912 may be inserted when inner mouthpiece member 1912 is disposed within mouthpiece housing 20. This channel acts as a guide passage for guiding nebulized particles of the drug solution from separator outlet 148 to outlet port 26 and also filters the particles.

Figure 18B:
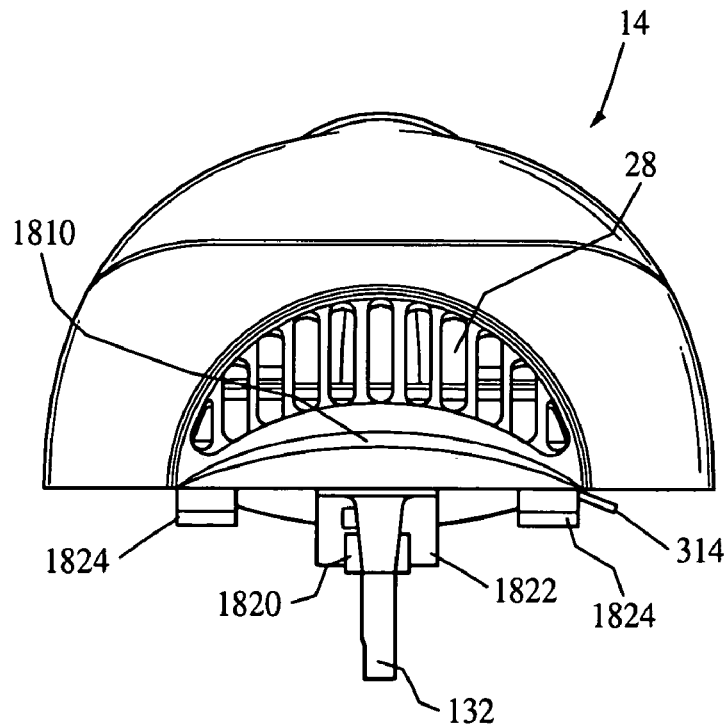
Figure 18D:
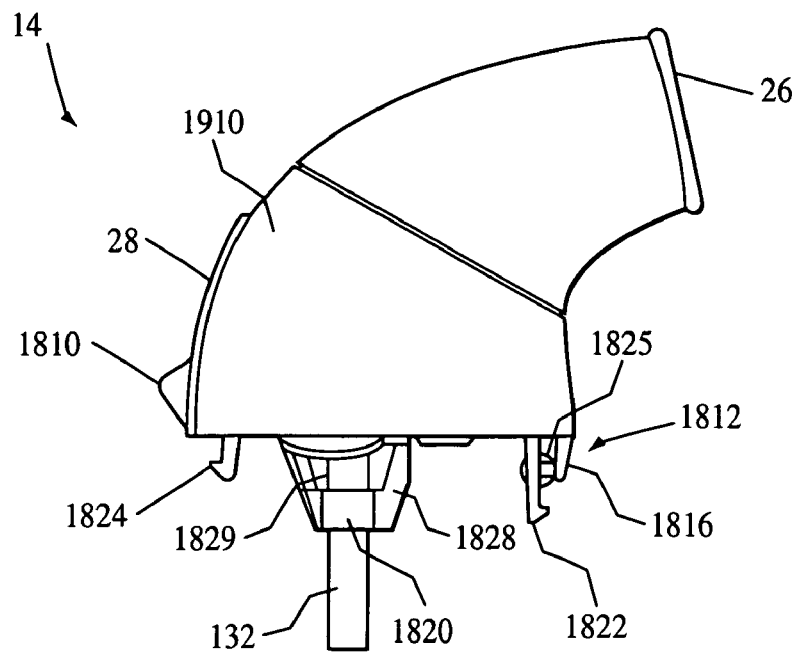

As best seen in FIGS. 18B and 18D, the rear of second housing member 1916 includes inlet port 28 and a finger rest 1810. At inlet port 28, intake gas is introduced into mouthpiece housing 20. Finger rest 1810 is a protrusion that extends outwardly from an outer surface of second housing member 1916. The finger rest is adapted to engage a finger (or hand) of the user as the user holds device 10 to receive nebulized particles of drug solution therefrom. Finger rest 1810 is disposed proximate to and beneath the inlet port 28, so that the finger or hand of the user holding device 10 is inhibited from inadvertently sliding over (and thus blocking) inlet port 28 during use.

As best seen in FIGS. 18A and 18D, the front of second housing member 1916 includes a convex-shaped, downwardly extended portion 1812. Extended portion 1812 is configured such that when mouthpiece module 14 is selectively coupled to intermediate module 16, extended portion 1812 fits into recessed portion 1120 in the intermediate module housing 22 (see FIG. 1B). Extended portion 1812 includes a depressible surface 1816 that may be depressed by the user to selectively decouple mouthpiece module 14 from intermediate module 16, as will be described below with greater particularity. Reinforcement ridges 1924 inside the second housing member 1916 (see FIG. 19A) provide reinforcement to second housing member 1916 at a side opposite extended portion 1812. The reinforcement of second housing member 1916 provided by reinforcement ridges 1924 enables the user to squeeze second housing member 1916 to flex depressible surface 1816 without simultaneously deforming the opposite side of second housing member 1916. This reduces the amount of force the user must apply in squeezing second housing member 1916 to adequately deform extended portion 1812 for coupling or uncoupling modules 14 and 16 because all (or substantially all) of the force applied by the user is used to deform depressible surface 1816, and not both depressible surface 1816 and the opposite of second housing member 1916.

Figure 18C:
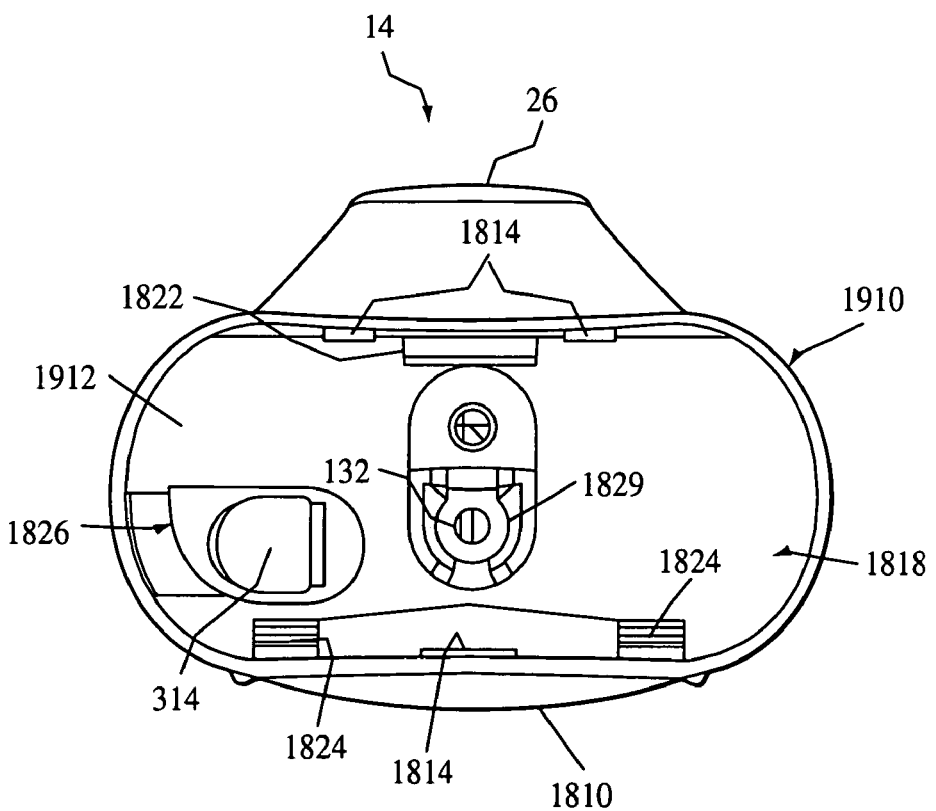

As shown in FIG. 18C, inner mouthpiece member retaining tabs 1814 are provided at opposing sides of mouthpiece housing 20. Inner mouthpiece retaining tabs 1814 secure inner mouthpiece member 1912 within mouthpiece housing 20. Specifically, the flexing capability of the housing member 1916 allows a substantially flat base portion 1917 of the inner mouthpiece member 1912 to ride over the retaining tabs 1814 and be retained thereby. That is, when the inner mouthpiece member 1912 is inserted upwardly into the outer mouthpiece housing 20, the outer edges 1919 of the base portion 1917 are able to ride over the tabs 1814 and be retained thereby. In an alternate embodiment, the inner mouthpiece member can be secured to mouthpiece housing 20 by a snap-fit, a weld, an adhesive bond, or other mechanisms for securing housing parts to each other.

In one embodiment of the invention, the inner mouthpiece member 1912 comprises two molded portions that are subsequently secured to one another. For example, in FIG. 19A, a first structure member 1926 and a second structure member 1928 is shown. First structure member 1926 includes one or more grooves (not shown) disposed at a side of first structure member 1926 to be joined to second structure member 1928. Second structure member 1928 may include one or more projections 1930 disposed at a side of second structure member 1928 to be joined to first structure member 1926. First structure member 1926 and second structure member 1928 may be joined to form inner mouthpiece member 1912 such that projections 1930 may be received by the grooves. First structure member 1926 and second structure member 1928 may be secured to each other by one or more mechanisms for securing components to each other, such as, for example, a weld, an adhesive bond, a snap-fit, or other mechanisms for securing components to each other.

Inner mouthpiece member 1912 includes a stop member 1932, a guide tube collar 1820, a baffle 310, the previously described base portion 1917, and separator structure 124. The base portion 1917 forms part of a cup interface portion 1818 that enables mouthpiece module 14 to be selectively coupled to intermediate module 16. In one embodiment, the cup interface portion 1818 includes a biased barbed tab 1822, and one or more rigid barbed tabs 1824. Biased barbed tab 1822 and rigid barbed tabs 1824 are disposed on cup interface portion 1818 such that biased barbed tab 1822 may engage front slot 1138 (see FIG. 11D) associated with intermediate module 16 and rigid barbed tabs 1824 engage rear slots 1140 associated with intermediate module 16 to selectively couple mouthpiece module 14 to intermediate module 16.

Barbed tabs 1822 and 1824 are engaged with slots 1138 and 1140 by inserting rigid barbed tabs 1824 into rear slots 1140 and pivoting mouthpiece module 14 with respect to intermediate module 16 (or vice versa), about a fulcrum formed by the engagement between rigid barbed tabs 1824 and rear slots 1140, until biased barbed tab 1822 approaches front slot 1138. As biased barbed tab 1822 approaches front slot 1138, a force may be applied to biased barbed tab 1822 at an outer side of biased barbed tab 1822 that deforms biased barbed tab 1822 to enable biased barbed tab 1822 to engage front slot 1138. After biased barbed tab 1822 engages front slot 1138, a stop 1825 provided on the tab 1822 to impede further pivoting of mouthpiece module 14, at which point the force may be released, thereby effectively coupling mouthpiece module 14 to intermediate module 16 as the barbs associated with barbed tabs 1822 and 1824 engage mouthpiece interface portion 1222 in which slots 1138 and 1140 are formed. To uncouple mouthpiece module 14 from intermediate module 16, a force can be applied to biased barbed tab 1822 at the outer side of biased barbed tab 1822 that deforms biased barbed tab 1822 such that the barb associated therewith may be disengaged from slot 1138, enabling mouthpiece module 14 to be pivoted with respect to intermediate module 16. Biased barbed tab 1822 may be disposed on cup interface portion 1818 such that the user may apply a force to biased barbed tab 1822 by depressing depressible surface 1816 of extended portion 1812 associated with mouthpiece housing 20.

As shown in FIG. 19A, stop member 1932 may be formed proximate to separator structure 124 on a same side of separator structure as inlet port 28. Stop member 1932 serves to engage an inner surface 1916 of the outer mouthpiece housing portion (see FIG. 22), as inner mouthpiece member 1912 is positioned and/or retained in mouthpiece housing 20. This limits upward movement of inner mouthpiece member 1912 into mouthpiece housing 20.

Intake gas introduced into mouthpiece housing 20 through air intake vent 28 is separated by baffle 310. Specifically, referring to FIG. 4A, when a user inhales through outlet port 26, a first portion of the intake gas from the atmosphere flows above baffle 310, directly to outlet port 26. A second portion of the intake gas flows below baffle 310 to be directed into the drug solution pool cup 1411 and through the separator structure 124 for delivery to the user. The intake gas is divided into the first portion and the second portion according to several considerations. For example, since the first portion of the intake gas provided directly from air intake vent 18 outlet port 20 travels over a less restricted path than the second portion of the intake gas that is directed into the drug solution pool cup 1411 and through the separator structure 124, the division of the intake gas between these two paths reduces an amount of suction that must be applied by the user in inhaling the nebulized particles. Another consideration includes avoiding a provision of an excessive amount of the intake gas into the drug solution pool cup 1411 and through the separator structure 124, which may interfere with the formation and delivery of the nebulized particles by creating a gas flow with too high a flow rate. The intake gas may be divided according to other considerations. In one embodiment, approximately 60% of the intake gas may be included in the first portion and the remaining approximately 40% of the intake gas may be included in the second portion, or the intake gas may be otherwise divided.

After the intake gas (e.g., from atmosphere) that is used for drug delivery passes below baffle 310, it passes through an opening 1826 formed in inner mouthpiece base portion 1917 (see FIG. 18C) and into the pool cup region 1411. The intake gas then travels back through base portion 1917, a central opening 1829 formed therein, and leading to separator inlet 312. The air intake then travels through separator regions 130 and 140 (see FIG. 3) and carries with it nebulized particles through outlet 26.

As discussed previously, the device 10 may optionally be provided with a one-way valve 314 within the drug delivery flow path. As can be seen in FIGS. 18C and 19A, in the present embodiment, the one-way valve 314 is disposed within the opening 1826. Valve tabs 1934 formed on the base region 1917 may interface with one or more peripheral grooves 1936 formed on one-way valve 314 such that one-way valve 314 may be secured into valve opening 1826. Thus, intake air that is drawn beneath the baffle 310 must pass through the valve 314 prior to entering into the drug solution pool cup and the separator inlet 312.

In one embodiment, one-way valve 314 is a passive valve. At a default or "normal" position, one-way valve 314 is open, enabling intake gas to pass freely therethrough from inlet port 28 to separator inlet 312. This normally open position enables nebulized particles generated at fountain 128 to be motivated to outlet port 26 when the device 10 is powered on. As a result, the open default position of one-way valve 314 enables device 10 to produce a visible aerosol at outlet port 26 when device 10 is activated without the user engaging device 10 at outlet port 26 to inhale. The presence, or absence, of the visible aerosol at outlet port 26 enables the user to determine whether device 10 is operating prior to engaging the mouth at outlet port 26. Being able to visualize the aerosol prior to inhalation may provide comfort to the user that the device 10 is functioning properly.

In one embodiment, one-way valve 314 will close when gas is introduced to device 10 at outlet port 26. This may occur, for example, when the user inadvertently exhales into device 10. Closing one-way valve 314 when gas is introduced to device 10 at outlet port 26 will inhibit gas from flowing in a reverse direction along the delivery flow path, which would force the drug solution that may be airborne within device 10 to be expelled via inlet port 28.

In one embodiment, the one-way valve 314 has a valve body defining an aperture 316, and a valve flap 318, integrally connected (by being integrally molded) with the body. The connection may be in the form of a "living hinge." Under typical operating circumstances, valve flap 318 may permit intake gas to flow through valve aperture 316 from inlet port 28 to separator inlet 312. As is illustrated in FIG. 4B, when gas is introduced into device 10 at outlet port 26, a resulting flow of gas and drug solution of sufficient velocity from separator inlet 312 to inlet port 28 will cause valve flap 318 to close, sealing (or substantially sealing) the delivery flow path. Sealing the delivery flow path in this manner will cause the gas introduced to housing 12 at outlet port 26 to remain above the inner housing base 1917 and to flow out of device 10 via inlet port 28 in a flow path that is reverse of the direct flow path.

It should be appreciated that any normally open one-way valve can be used. In one embodiment, a ball and spring type check valve may be used. In one embodiment, the one way valve may be electrically operated, such as by a solenoid. In such an embodiment, the one way valve may be normally closed, and may be opened when the user is engaging outlet port 26 to inhale. For example, the electrically operated valve may be opened based on an automated detection of engagement of outlet port 26 by the user, or the valve may be opened based on a user control.

As can be appreciated from FIGS. 18D and 19A, the guide tube 132 is fixed to guide tube collar 1820. Guide tube collar 1820 is supported by one or more collar struts 1828. Collar struts 1828 extend from separator structure 124 at separator inlet 312 to guide tube collar 1820. The central opening 1829 in the inner housing base member is of a larger diameter than the guide tube 132. Thus the drug delivery flow path from the drug solution cup 1411 passes through the central opening along a passage that is between the edge 2009 surrounding the opening 1829 and the exterior surface of guide tube 132. From the central opening 1829, the drug delivery flow path is able to enter into the separator inlet 312.

According to one embodiment of the invention, an inner diameter of guide tube 132 may be varied to provide control over one or more aspects of the nebulization of the drug solution. For instance, by varying the inner diameter of guide tube 132, a nebulized particle size delivered to the user, a flow rate of the drug solution delivered to the user, or other aspects of the nebulization may be controlled. In a non-limiting example, guide tube 132 may include an inner diameter of between 2 mm and 3 mm, with smaller inner diameters producing smaller nebulized particles and/or a lower flow rate, and larger inner diameters producing larger nebulized particles and/or a higher flow rate.

For example, in FIG. 20 the first guide tube 132, of a first inner diameter, may be selectively uncoupled from guide tube collar 1820. This may enable a second guide tube 2012, of a relatively smaller inner diameter, to be coupled to guide tube collar 1820 in place of first guide tube 2010. In this embodiment, the outer diameter of the guide tubes 132 and 2012 are the same, thus allowing each to be affixed to the same guide tube collar 1820. As a separate example, as illustrated by way of example in FIG. 21, a first mouthpiece module 2110 may include a first guide tube 2112, of a first inner diameter. First mouthpiece module 2112 may be selectively uncoupled from intermediate module 16 to enable a second mouthpiece module 2114, including a second guide tube 2116, of a smaller inner diameter, to be selectively coupled to intermediate module 16, thereby varying the inner diameter of the guide tube employed in device 10. In yet a third embodiment, the mouthpiece outer housing 20 may be used with different inner mouthpiece housings having associated the guide tube of different inner diameter.

Figure 20:
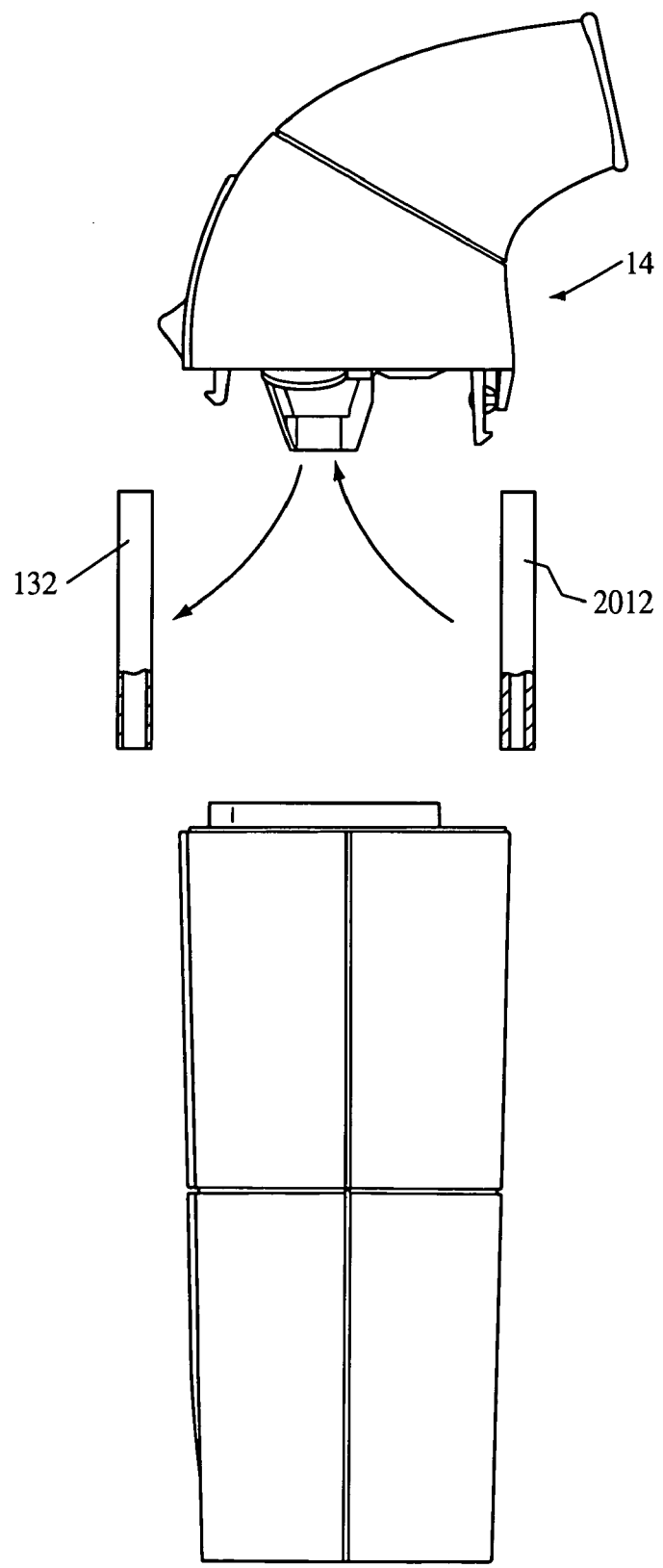
FIG. 20 is an illustration of the drug delivery device including interchangeable guide tubes in accordance with an embodiment of the invention.

In some embodiments, the flow rate and/or the size of the nebulized particles is adapted to the lung size of the user. This is because the flow rate and/or the size of the nebulized particles impact the location in the lungs of the user where the drug solution will be delivered. For example, in delivering the drug solution to the same region of two sets of lungs associated with two separate users with different lung sizes, the drug must travel different distances. In the embodiments shown in FIGS. 20 and 21, the guide tubes may be interchanged to optimize delivery of a single drug solution to the two separate users. In these instances, first mouthpiece module 2110, and second mouthpiece module 2114 may include other customizations for the two separate users.

Figure 21:
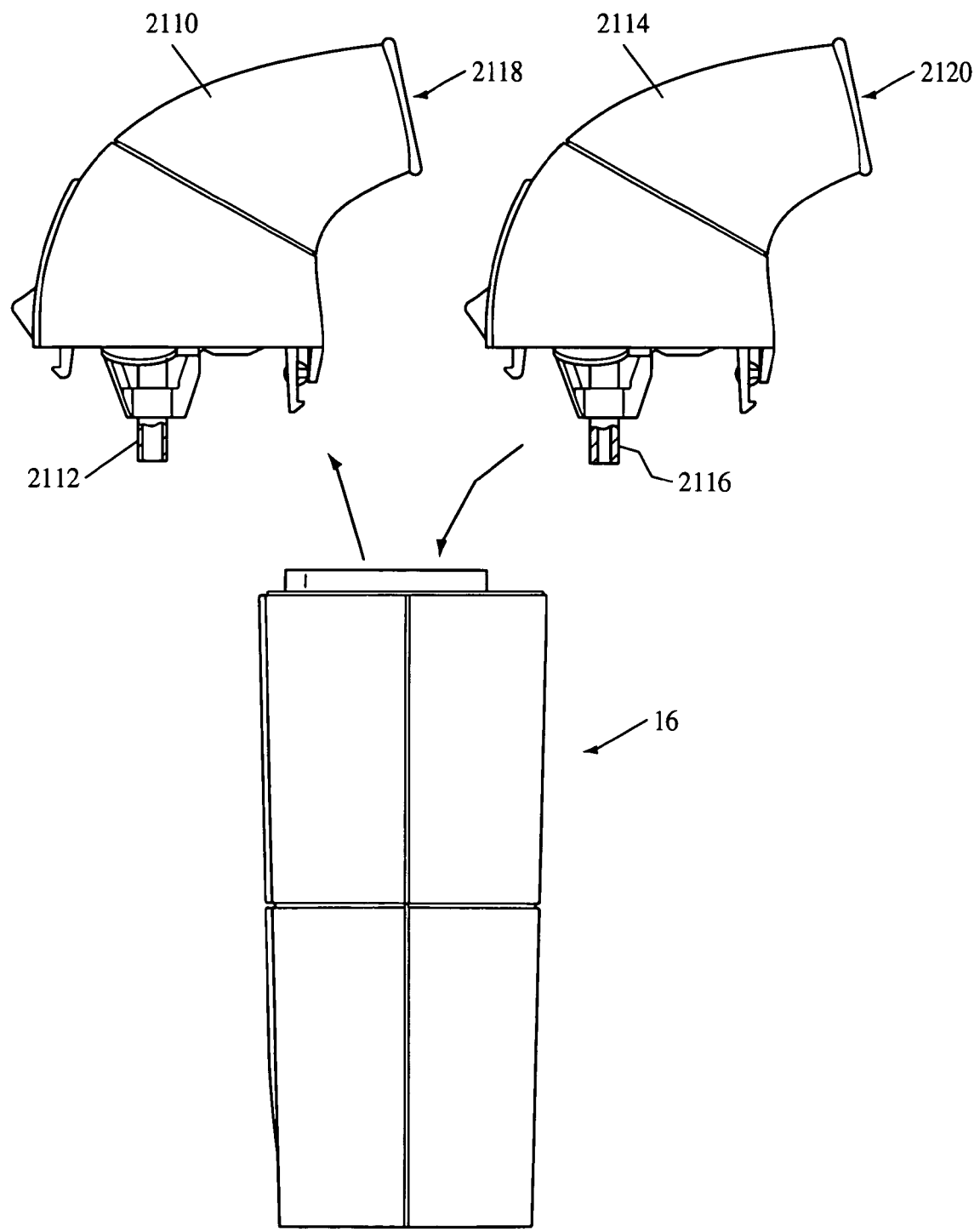
FIG. 21 is an illustration of the drug delivery device including interchangeable mouthpiece modules in accordance with an embodiment of the invention.

In a non-limiting example, illustrate by FIG. 21, first guide tube 2112 may be adapted for delivering the drug solution to a user with a smaller lung size, such as the lung size of a child, than second guide tube 2116, which may be adapted to the lung size of an adult. In this example, mouthpiece modules 2110 and 2114 may be further customized to the intended users by including a smaller first outlet port 2118 on first mouthpiece module 2110 than a second outlet port 2120 on second mouthpiece module 2114.

Figure 7:
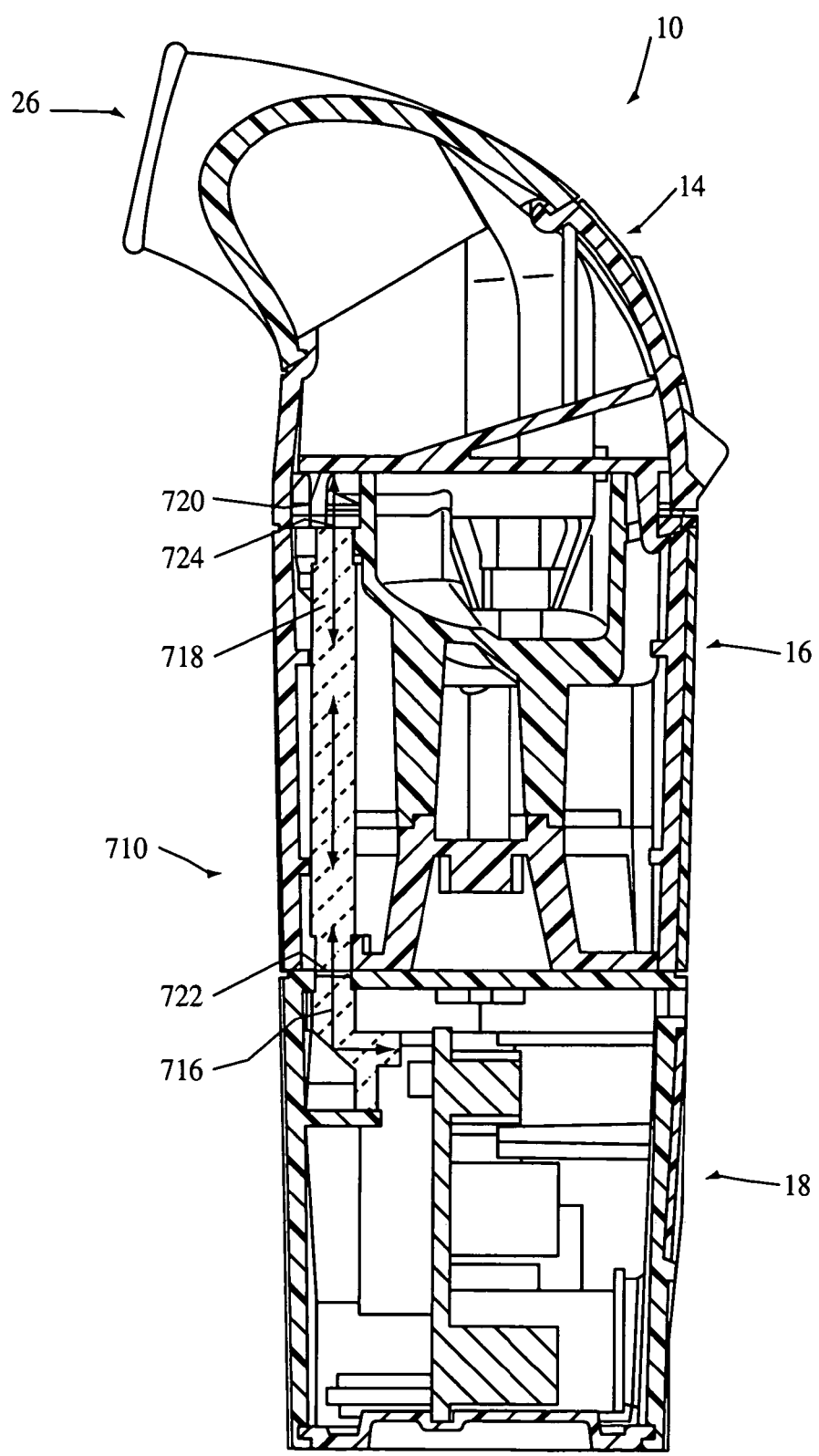
FIG. 7 is a cross-sectional view of the nebulizing device of FIG. 1B, taken along section line 7-7 of FIG. 1B, according to an embodiment of the invention.

As mentioned previously, and as can be appreciated from FIGS. 2, 8, 9A-9C, and 1A-E, modules 14, 16, and 18 may be selectively coupled to and decoupled from each other. That is, the module housing 20, the intermediate module housing 22, and the base module housing 24 are provided with interengaging structure that enables these housing portions to be coupled and decoupled, as will be described later in greater detail. Moreover, as shown in FIG. 7, in one embodiment, device 10 optionally includes an interlock detection system 710 that ensures that modules 14, 16, and 18 are satisfactorily coupled to each other prior to activation of device 10. In one embodiment, the interlock system 710 may include a signal transmitter carried by the housing, a signal receiver carried by the housing, and a conduit that transmits a signal from the transmitter to the receiver. When one of the modules is separated or misaligned from the adjoining module to prevent the signal from being transmitted from the transmitter to the receiver, and the aerosol generator is disabled when the signal is prevented from being transmitted from the transmitter to the receiver. For example, the presence or absence of the signal at the receiver may be transmitted to the control electronics, which may disable the aerosol generator, or transmit a deactivation control to the aerosol generator, in the absence of the signal.

In the illustrated embodiment, the signal transmitter is an infrared (IR) source 712, the receiver is an IR detector 714, and the conduit is an internally reflecting light pipe 716, 718 with mouthpiece surface 720 as will be described. Of course a variety of other signal transmitters/receivers could be used in accordance with the present invention that operate at different frequencies outside the Infrared band such as visible light or RF. In fact a multitude of different signals across the electromagnetic spectrum could be used without departing from the unique aspects of the present invention. The source 712 is disposed in the base module 18 and emits a signal along a detection path to the detector 714. The signal travels through base module light pipe 716 to a cup light pipe/base light pipe interface 722, disposed at the juncture between the base module 18 and intermediate module 16. When the intermediate module housing 22 is coupled to the base module housing 18, the cup/base light pipe interface 722 are joined in abutting relation, thus permitting radiation to pass from base light pipe 716 to cup light pipe 718. The signal passes through cup light pipe 718 to a mouthpiece/cup light pipe interface 724 carried by the mouthpiece housing 20. At mouthpiece/cup light pipe interface 724, the mouthpiece module 14 is provided with a reflective surface 720. Thus, when the mouthpiece housing 20 is coupled with the cup housing 22, the signal emitted from cup light pipe 718 is reflected by reflective mouthpiece surface 720 and retraces the optical path back to base module 18, where detector 714 receives the reflected radiation. If the modules 14, 16, and 18 are not satisfactorily coupled, the detection path will be broken, and the radiation will not be returned to the detector 714. Based on the absence of or insufficiency of radiation at detector 714, interlock system 710 will disable activation of device 10. For example, in one embodiment, the detector 714 is functionally coupled with the device control electronics, which disables the device 10 by preventing the aerosol generator (e.g., piezoelectric transducer) 118 from being activated when the signal conduit is broken.

In another contemplated embodiment, the transmitter sends a simple electrical signal that is transmitted through an electrical conduit from the base module 18, through the intermediate module 16 and to the mouthpiece module 14, where it may be detected by a signal receiver, or where it is then returned to a signal receiver in the base module. The signal receiver functionally cooperates with the device control electronics to disable the aerosol generator 118 when the signal is prevented from reaching the signal receiver. In such an embodiment, the respective interfaces between modules 14, 16, and 18 may comprise simple electrical contacts that are broken when a module is disengaged.

A variety of different switches could be used to create a signal interrupter that either makes or breaks contacts when the modules are disassembled or misaligned. The switch could be a mechanical switch using electrical contacts between the modules, or a push button switch that is actuated during assembly. Alternatively, the switch could utilize a magnetic field for actuation rather than mechanical contacts such as a reed switch or a magnet with a corresponding magnetic sensor such as a hall-effect sensor.

In another embodiment, a wireless proximity detector can be employed. In such an embodiment, a wireless transmitter sends a signal that may be received by a wireless receiver in the mouthpiece module. In this instance, the conduit may be considered the space through which the wireless signals are transmitted. When the receiver in mouthpiece housing is farther than a threshold distance from the transmitter, the conduit is broken as the signals can no longer be received by the receiver, and the control electronics will disable the aerosol generator 118.

One benefit to the interlock arrangement is when the base module 18 is coupled with the intermediate module 16, but before the mouthpiece module 14 is coupled with the intermediate module 16, the user cannot inadvertently activate the aerosol generator without the mouthpiece module 14 in place. By contrast, it should also be appreciated that when the mouthpiece module 14 is coupled with the intermediate module 16, but the base module 18 is disconnected from the intermediate module 16, inadvertent activation of aerosol generator 118 would have no effect on the drug solution because the control electronics of the base module 18 and power source would not be connected with the aerosol generator in the intermediate module 16. It can be appreciated, therefore, that in an embodiment that employs the mouthpiece module, and a signal module that contains all of the control electronics of the base module 18 and the aerosol generator of the drug solution pool of the intermediate module, then only an interlock detection between the mouthpiece module 14 and the rest of the assembly can be employed.

It should be appreciated that many of the principles and features described herein can be used in an embodiment of the present invention that does not employ the guide tube 132. In such a system, most of the volume of the drug solution within the device 10 is contained in a reservoir that feeds the drug solution to the pool region that rests on the aerosol generator 118 as the drug solution 116 becomes depleted. A valve system, such as a float valve, can be used to regulate or control distribution of the drug solution from the reservoir to the aerosol generator 118.

Figure 5:
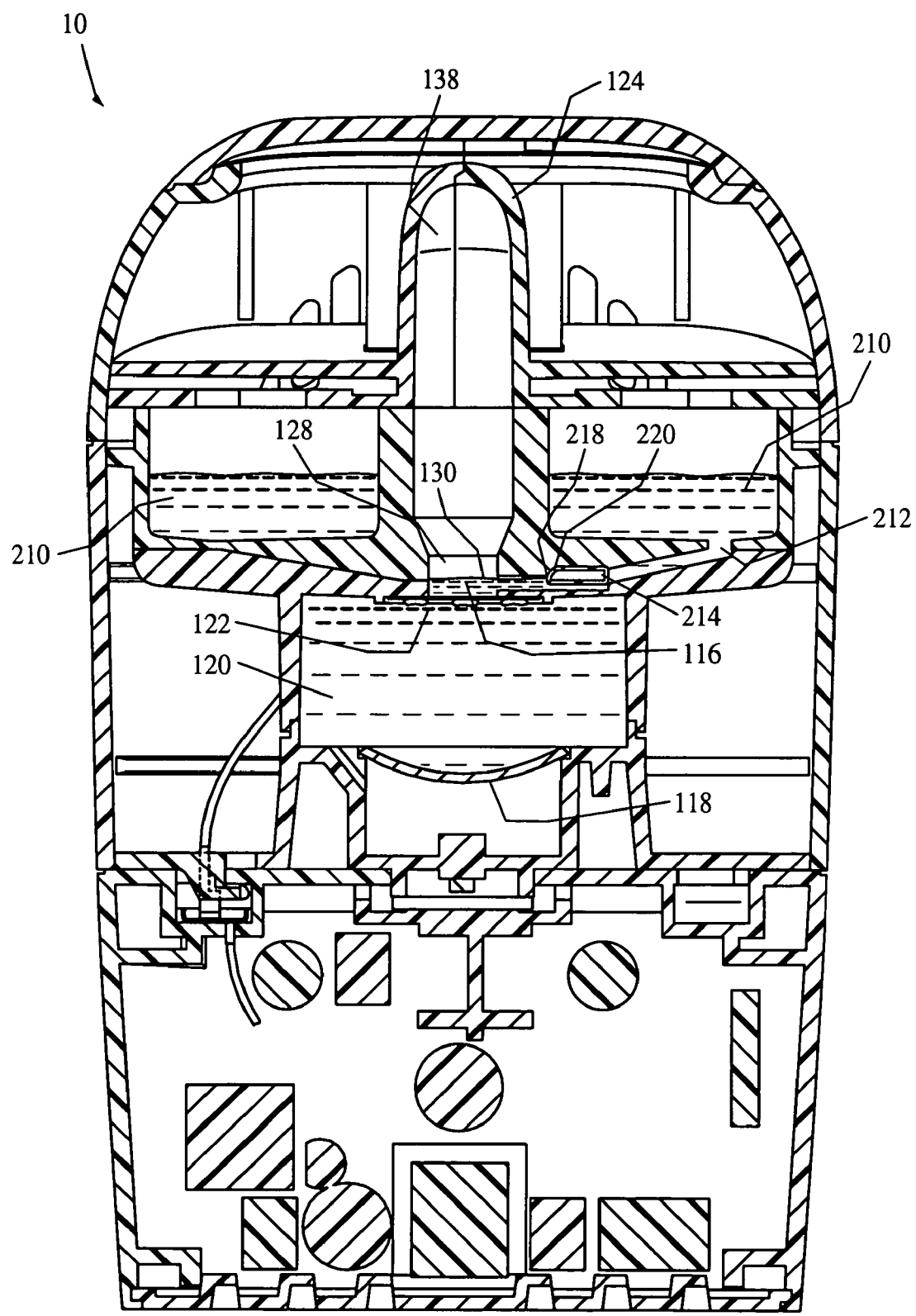
FIG. 5 is a cross-sectional view of the nebulizing device of FIG. 6, taken along cross-section line 5-5 of FIG. 6, in accordance with one embodiment of the invention.
Figure 6:
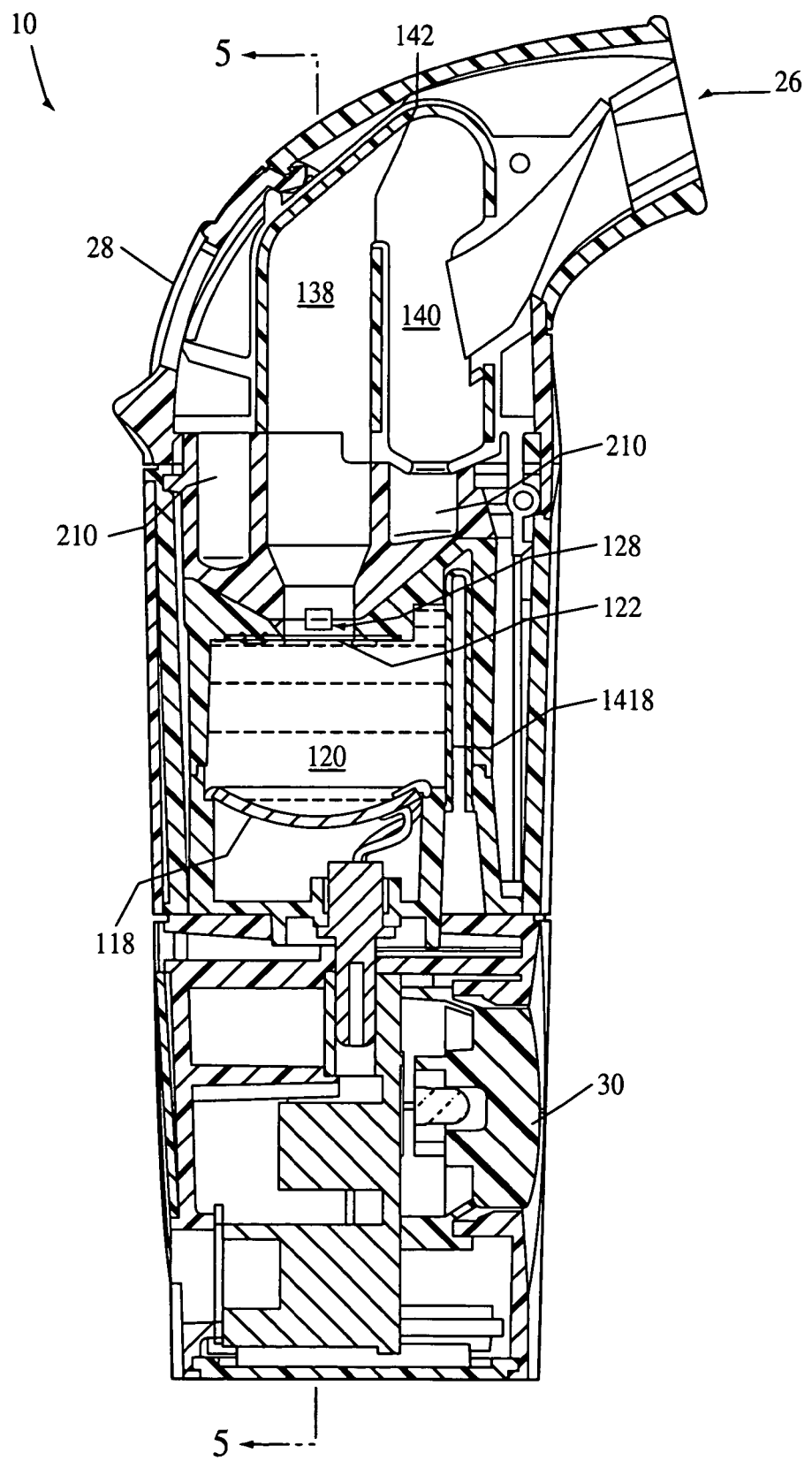
FIG. 6 is a cross-sectional view of the nebulizing device of FIG. 1B, taken along section line 6-6 of FIG. 1B, in accordance with an embodiment of the invention.

More particularly, in one embodiment illustrated in FIGS. 5 and 6, drug reservoir 210 may provide the drug solution to drug solution 116 via fill channel 212 to replenish the drug solution when the level of upper surface 130 of the drug solution drops due to nebulization, or other factors, thereby maintaining the level of upper surface 130 of the drug solution 116 at or proximate to the focal point of the acoustic waves generated by aerosol generator 118.

A float valve 214 may be positioned at fill channel opening 212 in drug solution 116 such that when the level of upper surface 130 rises, float 214, which is buoyant in the drug solution, rises up to block the drug solution from flowing into drug solution 116 from fill channel 212. However, when the level of upper surface 130 begins to drop, float valve 214 falls away from fill channel opening 212, thereby enabling the drug solution in fill channel 212 to flow into drug solution 116 until the level of upper surface 130 rises to a point where float 214 again blocks fill channel opening 212. Float valve 214 may include an angled float surface 218. Angled float surface 218 may interface with an angled device surface 220 to bias float valve 214 against fill channel opening 212 as float valve 214 rises. In one embodiment, float valve 214 is composed of a closed cell foam material.

The large droplets of the drug solution formed at fountain 128 are separated from the nebulized particles of the drug solution formed at fountain 128 by the separator structure 124. Subsequent to separation, the large droplets are returned to drug solution reservoir 210 via drug solution return 146. In one embodiment, drug solution reservoir 110 may be annular.

In some embodiments of the invention, separator structure 124 may provide a drug delivery path from fountain 128 to outlet port 26 for the nebulized particles formed at fountain 128. As the nebulized particles travel along the drug delivery path, separator structure 124 provides surfaces that separate nebulized particles formed at fountain 128 from the larger droplets formed by the drug solution propelled out of drug solution 116 prior to delivery of the nebulized particles to the user. Subsequent to separation from the nebulized particles, the larger droplets are returned to drug solution 116.

This arrangement is disclosed more fully in U.S. Patent Application Ser. No. 60/659,919 (now U.S. Patent Publication No. 2006-0201502), entitled NEBULIZING DRUG DELIVERY DEVICE WITH INCREASED FLOW RATE, filed on even date herewith and hereby incorporated by reference in its entirety.

Figure 22:
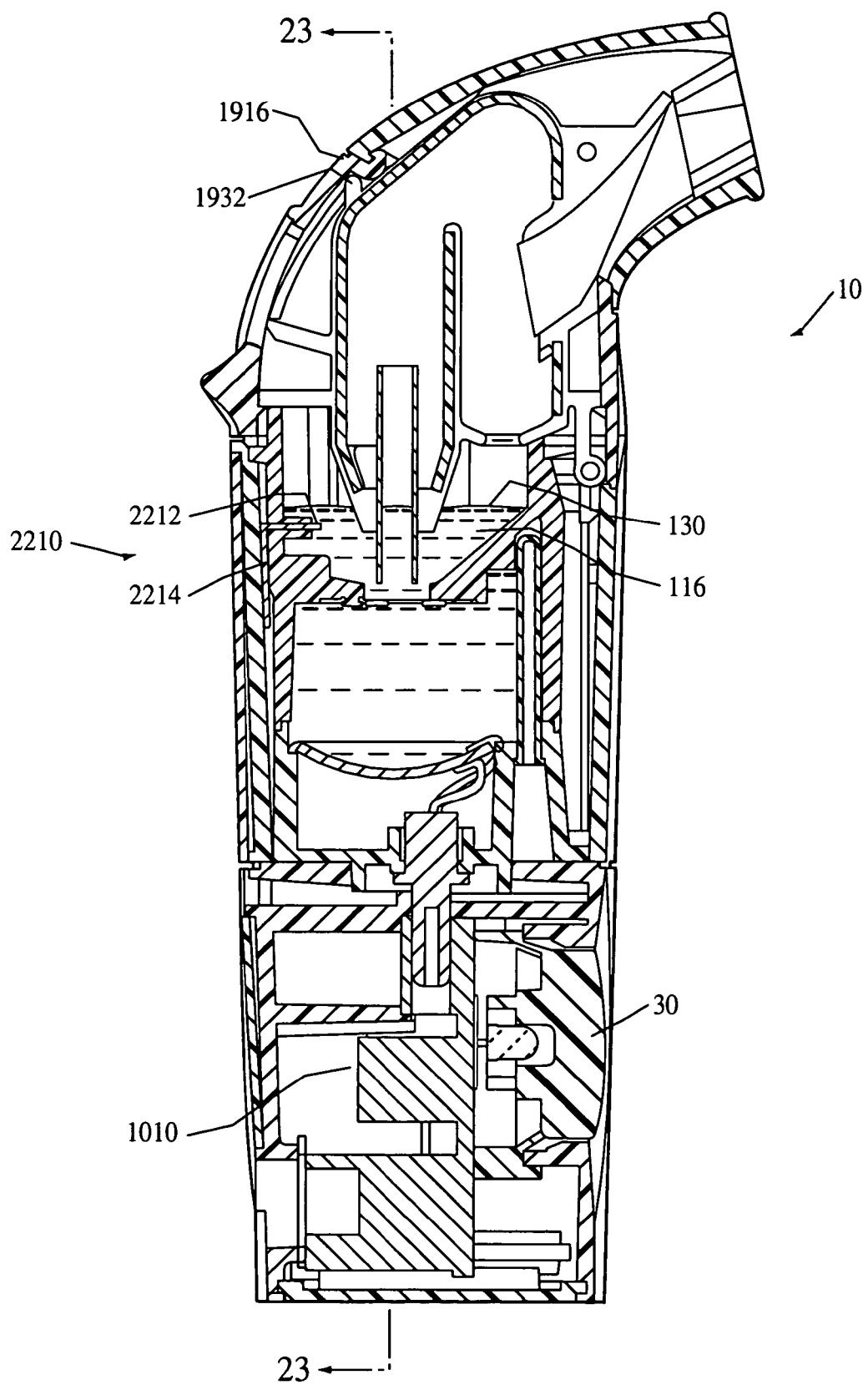
FIG. 22 is a cross-sectional view of the nebulizing device of FIG. 1B, taken along section line 22-22 of FIG. 1B, according to an embodiment of the invention.
Figure 23:
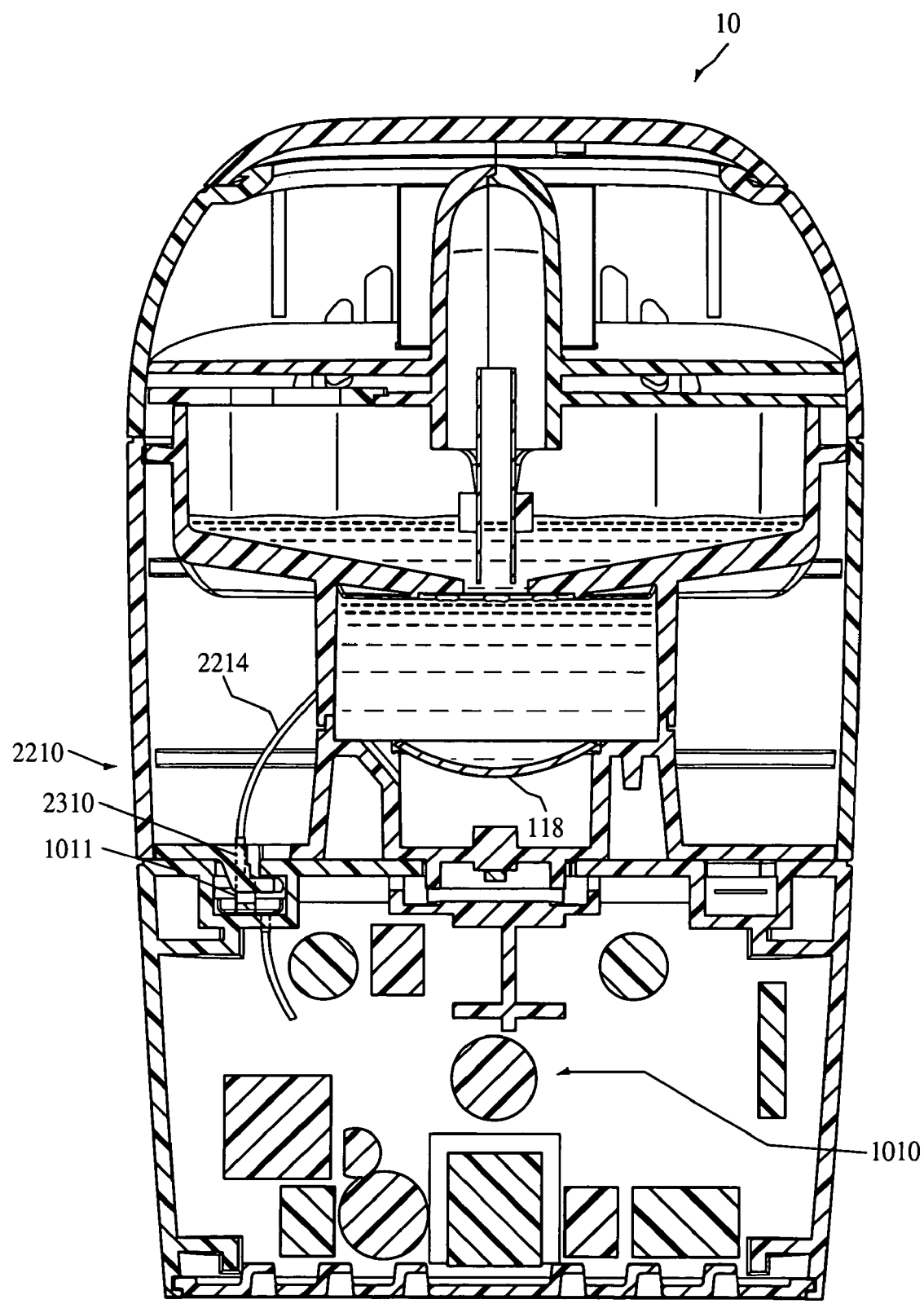
FIG. 23 is a sectional view of the nebulizing device of FIG. 22, taken along section line 23-23 of FIG. 22, in accordance with an embodiment of the invention.

FIGS. 22 and 23 illustrate an optional embodiment of device 10 that includes a drug solution detection system 2210. Drug solution detection system 2210 detects if the amount of drug solution 116 falls below a threshold level based on detection of an AC electrical signal detected in drug solution 116. Drug solution detection system may include a probe 2212, and a signal lead 2214.

Probe 2212 is positioned to detect the AC signal generated by the AC applied to the aerosol generator. Of course the signal could be generated by various other devices. In other words, the drug solution itself may act as a conduit for the AC signal that conducts the AC signal to probe 2212. When the upper surface 130 of the drug solution 116 falls below the threshold level, the drug solution will no longer act be able to deliver the AC signal to probe 2212. Although probe 2212 is illustrated as being disposed within drug solution 116, detecting the AC signal directly, in other embodiments, probe 2212 may be disposed in contact with an outer surface of a wall of drug solution pool cup 1411 and may detect the AC signal capacitively through the wall.

The AC signal (or lack thereof) detected by probe 2212 may be relayed to control electronics 1010 via signal lead 2214. At base module interface 1112, signal lead includes a lead connector 2310 disposed within tabbed extrusion 1132 that transmits the AC signal to control electronics via leaf spring 1011.

In one embodiment, when the AC signal is not detected, control electronics 1011 may automatically deactivate device 10. For example, aerosol generator 118 may be deactivated. Or, control electronics 1011 may activate an alert, such as, for example, a visual or audible indicia, that may warn the user that upper level 130 of the drug solution may have dropped below the threshold level.

The threshold level as contemplated herein can be virtually "empty". However, it may be desirable for the threshold level to be some drug solution volume above empty, to allow the user sufficient warning that the drug solution is near depletion. In addition, when the drug solution volume reaches below a certain level, its thermal mass also drops below a threshold that may make it more susceptible to temperature changes in the environment or due to components within the device itself. Such temperature changes may be undesirable, as it may alter the effectiveness of certain drug solutions. In one non-limiting example, it may be desirable in some embodiments of the present invention to provide the device 10 with a heater that heats the drug solution 116. Such a heating arrangement may be desirable to lower the viscosity of the drug solution pool, particularly when using a drug solution of a high viscosity. Such a heater may be provided in contact with the drug solution 116 itself, or surrounding the drug pool cup region 1411, as described in previously mentioned co-pending U.S. Patent Application Ser. No. 60/659, 919 (now U.S. Patent Publication No. 2006-02015021, filed on even date herewith and entitled NEBULIZING DRUG DELIVERY DEVICE WITH INCREASED FLOW RATE, and which is incorporated by reference in its entirety. In the event that the amount of drug solution drops below a threshold level, the thermal mass of the drug solution 116 may be subject to over heating. This may be prevented by disabling the aerosol generator 118 through use of the control electronics 1011 when the amount of drug solution drops below a threshold level as described above.

In another embodiment, it is contemplated two different drug solution levels may be detected. In such a system, a first low level is detected and provides either an audible or visual alarm to the user. This may prompt the user to refill the device 10 with drug solution. At this first low level point, however, the drug solution may not be sufficiently low to cause device 10 to be disabled, and the aerosol generator will continue to function. At a second low level point (e.g., when the drug solution 116 is of a less than desirable thermal mass) the system control electronics 1011 will then disable the aerosol generator. In such a dual level detection arrangement, it is contemplated that the control electronics can sense two different current levels transmitted through the drug solution 116, as the current level decreases with the increased resistance due to drug solution depletion. In another embodiment, two or more different probes are provided for detecting the two or more different drug levels.

It should also be appreciated that many of the principles of the present invention can be employed without a level detector, or with a known, conventional level detector.

It should also be appreciated that many of the principles of the present invention can be applied to a dual system that employs more than one aerosol generator 118. This may be useful again where high viscosity drug solution is being used, in order to increase the amount of drug that can be delivered. This dual arrangement is also disclosed in the aforementioned Application No. 60/659,919, and has been incorporated herein by reference.

In addition to detecting drug level, probe 2212 could be used for a variety of other unique purposes. First, probe 2212 could be used to detect if cup region 1411 has been breached (including barrier 122 or separating wall 1413). If breached, probe 2212 would be able to detect the change in the signal. Secondly, probe 2212 could be used as a sensor to detect the operation of aerosol generator 118. For instance, in the event that the aerosol generator is a piezoelectric device, it has been found that the amplitude of the detected AC shifts as the frequency applied to the piezoelectric device changes. It is preferred to operate the device at its resonant frequency which may vary from component to component. The resonant frequency corresponds with the maximum amplitude of the AC signal. Therefore, the resonant frequency can be identified by locating the maximum amplitude. In essence, this process is tuning the device. In the preferred embodiment, the resonant frequency occurs somewhere between 2.3 to 2.7 MHz. To find the optimum operating frequency of the device 10, the detected AC may be analyzed as the AC is cycled from frequency to frequency.

Alternatively, rather than using probe 2212, the operation of the piezoelectric device can be detected without probe 2212 by measuring the current drawn by the piezoelectric device. The current drawn by the piezoelectric device increases as the piezoelectric device approaches its resonant frequency. Once again, the frequency of the AC may be cycled from frequency to frequency to determine the frequency that results in the maximum current draw. In the preferred embodiment, the maximum frequency occurs somewhere between 2.3 to 2.7 MHz. Although this process could be performed at anytime, the inventors presently consider it to be desirable to perform this diagnostic at startup each time the device is turned on. Once the optimum frequency for the device is determined, this value may be stored in memory in electronics 1010.

It should also be appreciated that many of the principles of the present invention can be applied to a system designed for implementation within a ventilator circuit. This may be useful again where high viscosity drug solution is being used, in order to increase the amount of drug that can be delivered. Such an embodiment is disclosed in the U.S. Patent Application Ser. No. 60/659,782 (now U.S. Patent Publication No. 2006-0201500), entitled NEBULIZING DRUG DELIVERY DEVICE FOR VENTILATOR, filed on an even date herewith, and which is incorporated by reference, in its entirety.

Figure 24:
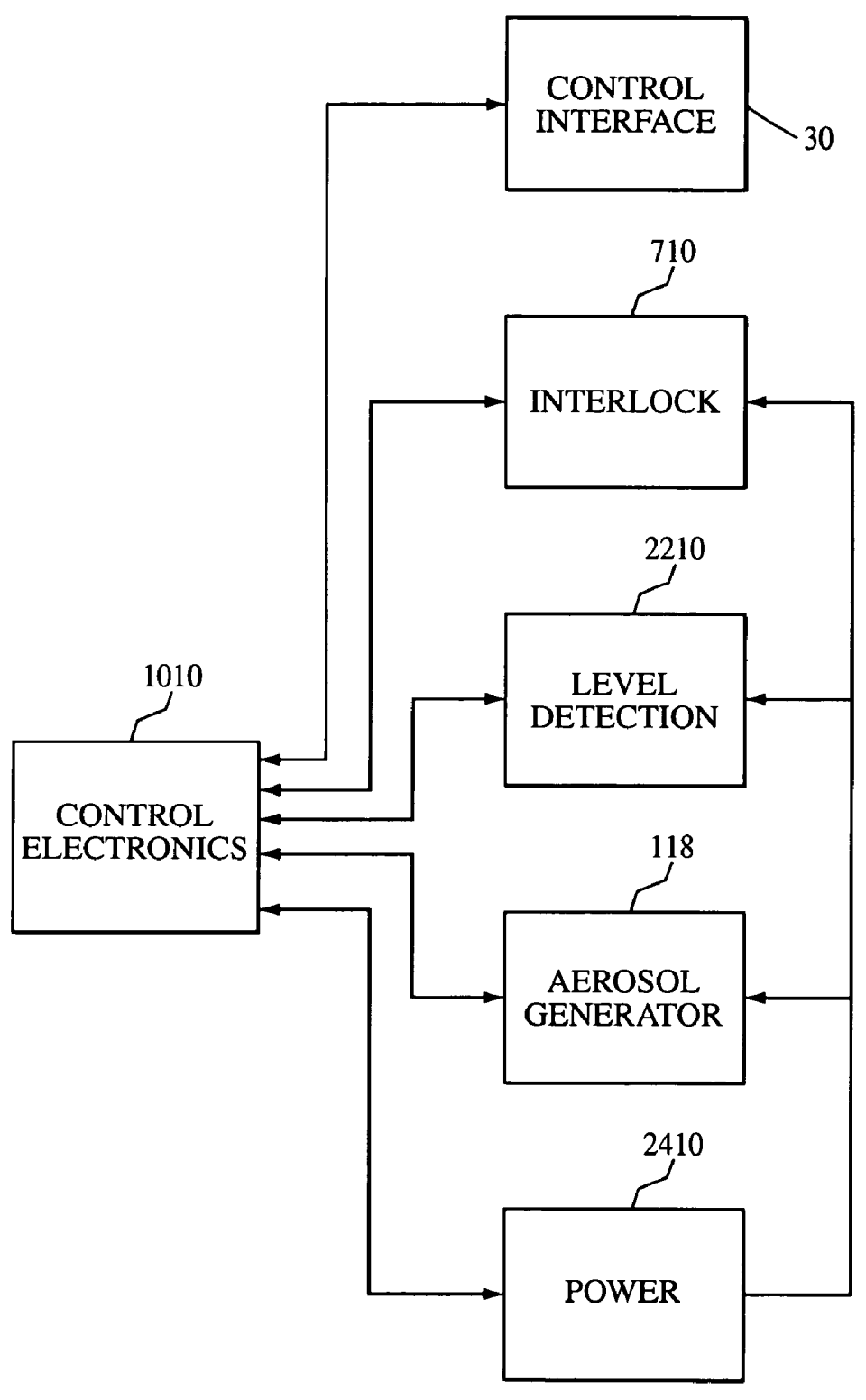

Referring to FIG. 24, an exemplary illustration of an electrical schematic representation of device 10 is provided. Control electronics 1010 are operatively linked with various components of device 10, such as, for example, control interface 30, a power source 2410 (this may include the power source coupled to device 10 via power interface 910, and/or an internal power source), aerosol generator 118, level detection system 2210, interlock system 710, and/or other components. The various components transmit signals to control electronics 1010 and/or receive control signals from control electronics 1010.

FIG. 25 illustrates an exemplary method of controlling a handheld nebulizing drug delivery device. Various electronic components within the device may initiate and/or execute some or all of the operations of the method.

The method includes an operation 2510 at which an activation command is received. The activation command may be initiated by a user that is using the device via, for example, a control interface, or may be automatically generated.

At an operation 2512, a determination is made as to whether one or more device modules included in the device are properly coupled. For example, a signal, emitted by a signal transmitter, may be received at a signal receiver. If the signal receiver does not receive the signal, the device modules are not properly coupled, and the method proceeds to an operation 2514. At operation 2514, an aerosol generator is deactivated. This includes both maintaining the current operating state of the aerosol generator if the aerosol generator is currently deactivated, and deactivating a currently activated aerosol generator. The deactivation of the aerosol generator prevents the device from generating, or attempting to generate, nebulized particles of drug solution for delivery to the user.

If, at operation 2516, the determination is made that the device modules are properly coupled based on, for example, reception of the signal by the signal receiver, then the method proceeds to an operation 2516. At operation 2516, the aerosol generator is activated. This includes both maintaining the current operating state of the aerosol generator if the aerosol generator is currently activated, and activating a currently deactivated aerosol generator. The activation of the aerosol generator enables the device to generate nebulized particles of drug solution for delivery to the user.

The method includes an operation 2518, at which a determination is made as to whether a threshold amount of drug solution is present in the device for nebulization. In some instances, this determination includes monitoring a signal of a probe associated with a pool of drug solution held within the device. The probe receives the signal from the aerosol generator through the pool of drug solution so long as the pool of drug solution includes an amount of the drug solution greater than the threshold amount, but does not receive the signal once the amount of the drug solution in the pool of drug solution falls below the threshold amount. If the signal is not received by the probe, signifying that the amount of the drug solution in the pool of drug solution is below the threshold amount, the method proceeds to operation 2514.

If, at operation 2518, the signal is received by the probe, signifying that the amount of the drug solution in the pool of drug solution is above the threshold amount, the method proceeds to an operation 2520. At operation 2520, a determination is made as to whether a deactivation command has been received. A deactivation command may be initiated by a user that is using the device via the control interface. If a deactivation command has been received, the method proceeds to operation 2514.

If, at operation 2520, a deactivation command has not been received, the method proceeds to operation 2522. At operation 2522, a determination is made as to whether the aerosol generator has been activated for a time that exceeds a time out period. The time out period may be automatically determined, or may be set by the user. The time out period may be set to protect various electronic components within the device from excessive stress, dose of the drug, or according to other considerations. If the time out period has been exceeded, the method proceeds to operation 2514. If the time out period has not been exceeded, the method returns to operation 2512.

It can thus be appreciated that embodiments of the present invention have now been fully and effectively accomplished. The foregoing embodiments have been provided to illustrate the structural and functional principles of the present invention, and are not intended to be limiting. To the contrary, the present invention is intended to encompass all modifications, alterations, and substitutions within the spirit and scope of the appended claims.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A nebulizing drug delivery device, comprising:
   a housing having an inlet and an outlet;
   an aerosol generator in communication with a fluid, wherein the aerosol generator comprises a concave ultrasonic generator for generating an acoustic wave;
   a barrier between the fluid and a pool of drug solution provided within the housing to isolate the fluid from the pool of drug solution, wherein the aerosol generator operates to form nebulized particles of the pool of drug solution that can be communicated to a user through the outlet, wherein at least a portion of the barrier is formed from polyetheretherketone; and
   a guide tube having a first end and a second end; and
   a support structure that holds the guide tube at a fixed position and orientation with respect to the housing such that the guide tube is spaced apart from the aerosol generator with the first end disposed within the pool of drug solution, wherein acoustic waves generated by the aerosol generator are focused in the drug solution such that a fountain of the drug solution is formed proximate the second end of the guide tube, wherein a majority of the nebulized particles are generated towards an upper end of the fountain, wherein the housing includes a mounting surface, and wherein the barrier is sealed to the mounting surface via thermal staking.

2. A nebulizing device according to claim 1, wherein the barrier is formed from two parts including a first part and a second part having an opening sealed with the first part, wherein the first part is sealed with the second part such that the opening generally defines a central portion of smaller thickness.

3. A nebulizing device according to claim 2, wherein the first part is sealed with the second part via an ultrasonic weld.

4. A nebulizing device according to claim 3, wherein a portion of the barrier is adhered to the mounting surface by a silicone based adhesive.

5. A nebulizing device according to claim 3, wherein a portion of the barrier has a plurality of holes formed therein, and wherein the mounting surface comprises a plurality of projections that are received within the holes, and wherein the projections are deformed in a manner that secures the barrier to the mounting surface.

6. A nebulizing device according to claim 5, wherein the mounting surface and the projections are formed from a polycarbonate material that can be melted so as to be deformed.

7. A nebulizing device according to claim 6, wherein the barrier is formed from polyetheretherketone.

* * * * *